United States Patent [19]
McAdam et al.

[11] Patent Number: 5,851,761
[45] Date of Patent: Dec. 22, 1998

[54] PROBES, KITS AND METHODS FOR THE DETECTION AND DIFFERENTIATION OF MYCOBACTERIA

[75] Inventors: Ruth Anne McAdam, Bronx, N.Y.; Jeremy Watson Dale, Guildford, United Kingdom; Zainul Fadziruddin Bin Zainuddin, Penang, Malaysia; David Catty, Birmingham, England

[73] Assignee: Cogent Limited, United Kingdom

[21] Appl. No.: 160,524

[22] Filed: Dec. 1, 1993

Related U.S. Application Data

[62] Division of Ser. No. 752,661, filed as PCT/GB90/00276 Feb. 22, 1990, abandoned.

[30] Foreign Application Priority Data

| Feb. 22, 1989 | [GB] | United Kingdom | .................... | 8903968 |
| Jan. 9, 1990 | [GB] | United Kingdom | .................... | 9000411 |

[51] Int. Cl.$^6$ ...................................................... C12Q 1/68
[52] U.S. Cl. ............................................... 435/6; 536/23.7
[58] Field of Search ................... 435/6, 253.1; 536/23.7

[56] References Cited

FOREIGN PATENT DOCUMENTS

| 2065424 | 3/1991 | Canada . |
| 8911665 | 9/1989 | France . |
| 9002676 | 3/1990 | France . |
| 89 039689 | 2/1989 | United Kingdom . |
| 90 004110 | 1/1990 | United Kingdom . |
| 91/03558 | 3/1991 | WIPO . |

OTHER PUBLICATIONS

Journal of General Microbiology, vol. 135, No. 9, Sep. 1989, SGM (GB), Z.F. Zainuddin et al.: "Polymorphic repetitive DNA sequences in *Mycobacterium tuberculosis* detected with a gene probe from a Mycobacterium fortuitum plasmid".
Journal of Clinical Microbiology, vol. 265, No. 11, Nov. 1988, American Society for Microbiology, K.D. Eisenach et al.: "Repetitive DNA sequences as probes for *Mycrobacterium tuberculosis*".
Nucleic Acids Research, vol. 18, No. 1, Jan. 1990, Oxford Press, (GB) D. Thierry et al.: "IS6110, an IS–like element of *Mycobacterium tuberculosis* complex".
Biological Abstracts, vol. 87, 1989, (Philadelphia, PA, US), R. P. Prabhakara et al.: "Repetitive DNA sequences of *Mycrobacterium tuberculosis*: Analysis of differential hybridization patterns with other mycrobacteria", Abstract 103147.
P.P. Reddi et al. "Repetitive DNA sequence of *Mycobacterium tuberculosis*: Analysis of differential hybridization pattern with other mycobacteria" *Int. J. Leprosy* 56:592–598 (1988).
M. Morita et al. "Recombinant vaccinia virus LC16m0 or LC16m8 that expresses hepatitis B surface antigen while preserving the attenuation of the parental virus strain"Vaccine 5:65–69 (1987).
S.M. Kerr et al. "Vaccinia virus encodes a polypeptide with DNA ligase activity" *Nucleic Acids Res.* 17:9039–9050 (1989).

A. Zabidi et al. Current Microbiology II, 235–240 (1984).
M. D. Cave et al. Molecular and Cellular Probes 5, 73–80 (1991).
McAdam et al., Mol. Microbiol. 4(9):1607–1613, 1990.
Rauzier et al., "Complete Nucleotide Sequence of pAL5000, A Plasmid from *Mycobacterium fortuitum*," *Gene*, 71:315–321 (1988).
Thierry et al., EMBL file access No. X17348 and GenBank access No. M29899 for "*Mycobacterium tuberculosis*". (undated).
Ausubel et al. (Eds.), "Hybridization with Radioactive Probes," *Current Protocols in Molecular Biology*, vol. 1, John Wiley & Sons, Inc., (2 pages) (1994).
Ausubel et al. (Eds.), "Screening of Recombinant DNA Libraries," *Short Protocols in Molecular Biology*, Third Edition, John Wiley & Sons, Inc., pp. 6–1–6–3 (1995).
Kent et al., "Demonstration of Homology between IS6110 of *Mycobacterium tuberculosis* and DNAs of Other Mycobacterium spp.," *Journal of Clinical Microbiology*, 33(9):2290–2293 (1995).
Gillespie et al., "Restriction Fragment Length Polymorphism Analysis of *Mycobacterium tuberculosis* Isolated from Patients with Pulmonary Tuberculosis in Northern Tanzania," *Transactions of the Royal Society of Tropical Medicine and Hygiene*, 89:335–338 (1995).
Maniatis et al., "Hybridization of DNA or RNA Immobilized on Filters to Radioactive Probes," *Molecular Cloning: A Laboratory Manual*, pp. 324–328 (1982).
Product Information Brochure, "Rapid Hybridization Buffer: Protocols for Rapid Filter Hybridizations," Amersham, pp. 1–23. (undated).
Jackson et al., "The *Mycobacterium tuberculosis* Purine Biosynthetic Pathway: Isolation and Characterization of the purC and purL Genes," *Microbiology*, 142: 1–9 (1996).
Torrea et al., "Chromosomal DNA Fingerprinting Analysis Using the Insertion Sequence IS6110 and the Repetitive Element DR as Strain–Specific Markers for Epidemiological Study of Tuberculosis in French Polynesia," *Journal of Clinical Microbiology*, 33(7):1899–1904 (1995).
Bjorvatn, B. (Ed.), "Reports of the Expert Panels" *Vaccine*, 14(7):700–701 (1996).

Primary Examiner—Scott W. Houtteman
Attorney, Agent, or Firm—Walter H. Dreger; Jan P. Brunelle

[57] ABSTRACT

The invention provides nucleotide probes, kits and methods for the detection and differentiation of Mycobacteria. The gene probes, kits and methods are useful for the diagnosis of tuberculosis and/or for epidemiological study tools for investigating the progress of infections caused by Mycobacteria.

The gene probes as provided comprise part or all of nucleotide sequences provided in the soecification or an allele or a derivative of the nucleotide sequences.

The gene probes can distinguish between *M.tuberculosis*, *M.bovis* and BCG as well as being able to distinguish between different strains of *M.tuberculosis*. The probes do not show significant hybridisation to nucleic acids from *M.paratuberculosis*, *M.intracellulare*, *M.scrofulaceum*, *M.phlei*, *M.fortuitum*, *M.kansasii*, *M.avium*, *M.malnioense*. *M.flavescens*, *M.gordonae* and *M.chelonei*.

12 Claims, 15 Drawing Sheets

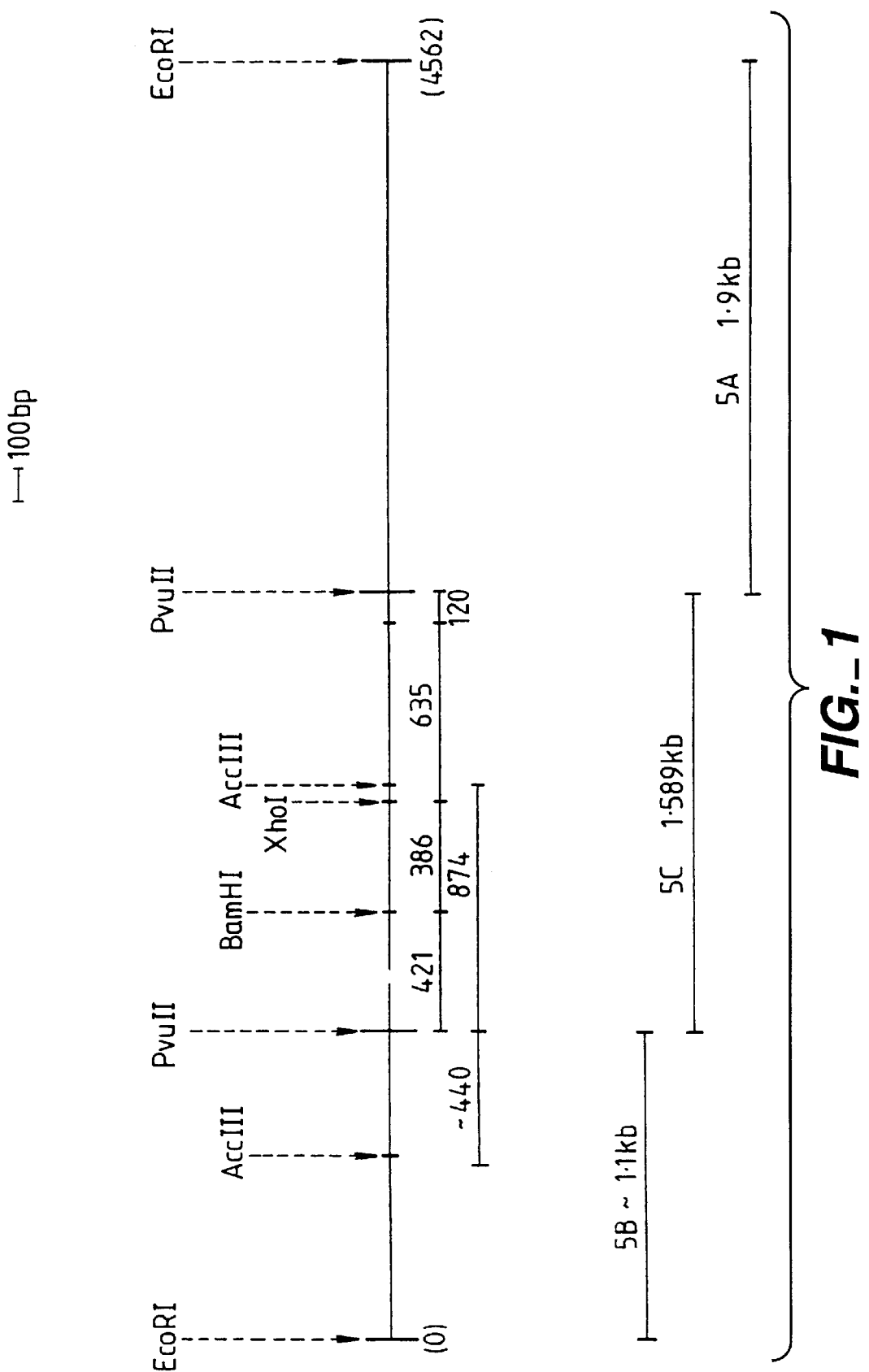
FIG._1

```
LeuThrGluLeuGlyValProIleAlaProSerThrTyrTyrAspHisIleAsnArgGlu
CTGACCGAGCTGGGTGTGCCGATCGCCCCATCGACCTACTACGACCACATCAACGGGAG
PvuII    10        20        30        40        50        60

ProSerArgArgGluLeuArgAspGlyGluLeuLysGluHisIleSerArgValHisAla
CCCAGCCGCCGCGAGCTGCGCGATGGCGAACTCAAGGAGCACATCAGCCGCGTCCACGCC
         70        80        90       100       110       120

AlaAsnTyrGlyValTyrGlyAlaArgLysValTrpLeuThrLeuAsnArgGluGlyIle
GCCAACTACGGTGTTTACGGTGCCCGCAAAGTGTGGCTAACCCTGAACCGTGAGGGCATC
        130       140       150       160       170       180

GluValAlaArgCysThrValGluArgLeuMetThrLysLeuGlyLeuSerGlyThrThr
GAGGTGGCCAGATGCACCGTCGAACGGCTGATGACCAAACTCGGCCTGTCCGGGACCACC
        190       200       210       220       230       240

ArgGlyLysAlaArgArgThrThrIleAlaAspProAlaThrAlaArgProAlaAspLeu
CGCGGCAAAGCCCGCAGGACCACGATCGCTGATCCGGCCACAGCCCGTCCCGCCGATCTC
        250       260       270       280       290       300

ValGlnArgArgPheGlyProProAlaProAsnArgLeuTrpValAlaAspLeuThrTyr
GTCCAGCGCCGCTTCGGACCACCAGCACCTAACCGGCTGTGGGTAGCAGACCTCACCTAT
        310       320       330       340       350       360

ValSerThrTrpAlaGlyPheAlaTyrValAlaPheValThrAspAlaTyrAlaArgArg
GTGTCGACCTGGGCAGGGTTCGCCTACGTGGCCTTTGTCACCGACGCCTACGCTCGCAGG
SalI 370       380       390       400       410       420

IleLeuGlyTrpArgValAlaSerThrMetAlaThrSerMetValLeuAspAlaIleGlu
ATCCTGGGCTGGCGGGTCGCTTCCACGATGGCCACCTCCATGGTCCTCGACGCGATCGAG
BamHI    430       440       450       460       470       480

GlnAlaIleTrpThrArgGlnGlnGluGlyValLeuAspLeuLysAspValIleHisHis
CAAGCCATCTGGACCCGCCAACAAGAAGGCGTACTCGACCTGAAAGACGTTATCCACCAT
         490       500       510       520       530       540

ThrAspArgGlySerGlnTyrThrSerIleArgPheSerGluArgLeuAlaGluAlaGly
ACGGATAGGGGATCTCAGTACACATCGATCCGGTTCAGCGAGCGGCTCGCCGAGGCAGGC
         550       560       570       580       590       600

IleGlnProSerValGlyAlaValGlySerSerTyrAspAsnAlaLeuAlaGluThrIle
ATCCAACCGTCGGTCGGAGCGGTCGGAAGCTCCTATGACAATGCACTAGCCGAGACGATC
         610       620       630       640       650       660

AsnGlyLeuTyrLysThrGluLeuIleLysProGlyLysProTrpArgSerIleGluAsp
AACGGCCTATACAAGACCGAGCTGATCAAACCCGGCAAGCCCTGGCGGTCCATCGAGGAT
         670       680       690       700       710       720

ValGluLeuAlaThrAlaArgTrpValAspTrpPheAsnHisArgArgLeuTyrGlnTyr
GTCGAGTTGGCCACCGCGCGCTGGGTCGACTGGTTCAACCATCGCCGCCTCTACCAGTAC
         730       740      SalI      760       770       780
```

FIG._2A

```
                CysGlyAspValProProValGluLeuGluAlaAlaTyrTyrAlaGlnArgGlnArgPro
                TGCGGCGACGTCCCGCCGGTCGAACTCGAGGCTGCCTACTACGCTCAACGCCAGAGACCA
                       790        800      XhoI   820         830        840

AlaAlaGly***
                GCCGCCGGCTGAGGTCTCAGATCAGAGAGTCTCCGGACTCACCGGGGCGGTTCAGGCCCC
                       850        860        870  AccIII880        890        900

GATGGTGTGCCCGGTGGTGATACGGGCACACCAGCACCAGGTTGGCCAGCTCGGTGGCCC
                       910        920        930        940        950        960

CACCGTCCTGCCAATGTCGGATGTGGTGGGCGTGCAAACCCCGGGTGGCCCCACAACCGG
                       970        980        990       1000       1010       1020

GAACCACACACGTGCGGTCGCGATGCTCAAGCGCACGACGCAACCGACGATTGATCTGAC
                      1030       1040       1050       1060       1070       1080

GAGTCGTTCGACCGCAGCCAATGACCTGCCCGTCACGTTCAAACCAGGCCTCAAAGGTGG
                      1090       1100       1110       1120       1130       1140

CATCACAGAGCAGATATCGGCGTTCGGACTCGCTGAGCAGCGGACCCAGGTGCAGGCCAG
                      1150       1160       1170       1180       1190       1200

CGGCACGCTCCTGCACGTCTAGATGCATCACCACGGTGGTGTGCTGCCCATGTGGCCGAC
                      1210       1220       1230       1240       1250       1260

GAGCCACCTCGGCGTCCCAGCCGGCCTCAACCAGACGCAGAAACGCCTCAACATTGCCCG
                      1270       1280       1290       1300       1310       1320

GCAACGGGGGCCGCTGATCCGACACACCGTCGCTGTTGTCGTGATCACGCTTGTACTCGG
                      1330       1340       1350       1360       1370       1380

CGATCAACGCATCCAGATGAGACTGCAACGCCGCATCGAACTTCGCCGCCTCCACGTCGA
                      1390       1400       1410       1420       1430       1440

AGCTTGATTCGCCAACAACTGAACTGCTCATCGGCGCTCCTGGTGATCGAGGGCCGCGGT
                      1450       1460       1470       1480       1490       1500

TCCGGCCGAAAATCCGGTTCGGGTTCGGGTCGCGGTTCCAACTTGAGCGCGGTCCGCAG
                      1510       1520       1530       1540       1550
```

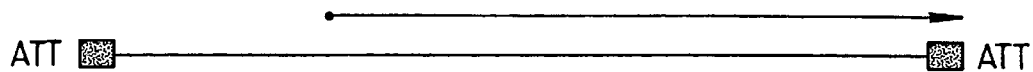
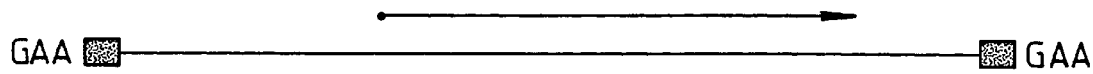
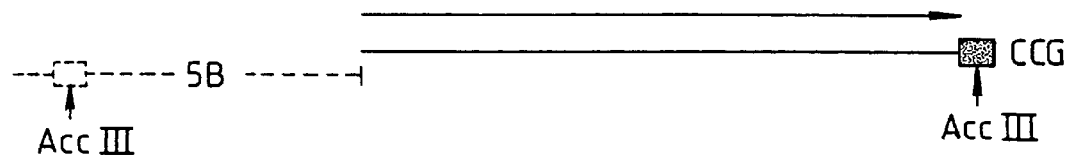
FIG._3

```
          10          20          30          40          50
CCTGAACCGC CCCGGCATGT CCGGAGACTC CAGTTCTTGG AAAGGATGGG
                       AccIII 60          70          80          90         100
GTCATGTCAG GTGGTTCATC GAGGAGGTAC CCGCCGGAGC TGCGTGAGCG 110         120         130         140         150
GGCGGTGCGG ATGGTCGCAG AGATCCGCGG TCAGCACGAT TCGGAGTGGG 160         170         180         190         200
CAGCGATCAG TGAGATCGCC CGTCTACTTG GTGTTGCTGC GCGGAGACGG 210         220         230         240         250
TGCGTAAGTG GGTGCGCCAG GCGCAGGTCG ATGCCGGCGC ACGGCCCGGG 260         270         280         290         300
ACCACGACCG AAGAATCCGC TGAGATAAAG CGCTTGCGGC GGGACAACGC 310         320         330         340         350
CGAATTGCGA AGGGCGAACG CGATTTTAAA GACCGCGTCG GCTTTCTTCG 360         370         380         390         400
CGGCCGAGCT CGACCGGCCA GCACGCTAAT TACCCGGTTC ATCGCCGATC 410         420         430         440         450
ATCAGGGCCA CCGCGAGGGC CCGATGGTT  TGCGGTGGGG TGTCGAGTCG 460         470         480         490         500
ATCTGCACAC AGCTGCCGA GCTGGGTGTG CCGATCGCCC CATCGACCTA
5B <---- PvuII----------> 5C 510         520         530         540         550
CTACGACCAC ATCAACCGGG AGCCCAGCCG CCGCGAGCTG CGCGATGGCG 560         570         580         590         600
AACTCAAGGA GCACATCAGC CGCGTCCACG CCGCCAACTA CGGTGTTTAC 610         620         630         640         650
GGTGCCCGCA AAGTGTGGCT AACCCTGAAC CGTGAGGGCA TCGAGGTGGC 660         670         680         690         700
CAGATGCACC GTCGAACGGC TGATGACCAA ACTCGGCCTG TCCGGGACCA 710         720         730         740         750
CCCGCGGCAA AGCCCGCAGG ACCACGATCG CTGATCCGGC CACAGCCCGT 760         770         780         790         800
CCCGCCGATC TCGTCCAGCG CCGCTTCGGA CCACCAGCAC CTAACCGGCT 810         820         830         840         850
GTGGGTAGCA GACCTCACCT ATGTGTCGAC CTGGGCAGGG TTCGCCTACG
                           Sal I
```

FIG._4A

```
       860        870        880         890        900
TGGCCTTTGT CACCGACGCC TACGCTCGCA GGATCCTGGG CTGGCGGGTC
                                 BamHI 910        920        930        940        950
GCTTCCACGA TGGCCACCTC CATGGTCCTC GACGCGATCG AGCAAGCCAT 960        970        980        990       1000
CTGGACCCGC CAACAAGAAG GCGTACTCGA CCTGAAAGAC GTTATCCACC 1010       1020       1030       1040       1050
ATACGGATAG GGGATCTCAG TACACATCGA TCCGGTTCAG CGAGCGGCTC 1060       1070       1080       1090       1100
GCCGAGGCAG GCATCCAACC GTCGGTCGGA GCGGTCGGAA GCTCCTATGA 1110       1120       1130       1140       1150
CAATGCACTA GCCGAGACGA TCAACGGCCT ATACAAGACC GAGCTGATCA 1160       1170       1180       1190       1200
AACCCGGCAA GCCCTGGCGG TCCATCGAGG ATGTCGAGTT GGCCACCGCG 1210       1220       1230       1240       1250
CGCTGGGTCG ACTGGTTCAA CCATCGCCGC CTCTACCAGT ACTGCGGCGA
      Sal I 1260       1270       1280       1290       1300
CGTCCCGCCG GTCGAACTCG AGGCTGCCTA CTACGCTCAA CGCCAGAGAC
                   Xho I 1310       1320       1330       1340       1350
CAGCCGCCGG CTGAGGTCTC AGATCAGAGA GTCTCCGGAC TCACCGGGGC
                                      AccIII

GGTTCAGG
```

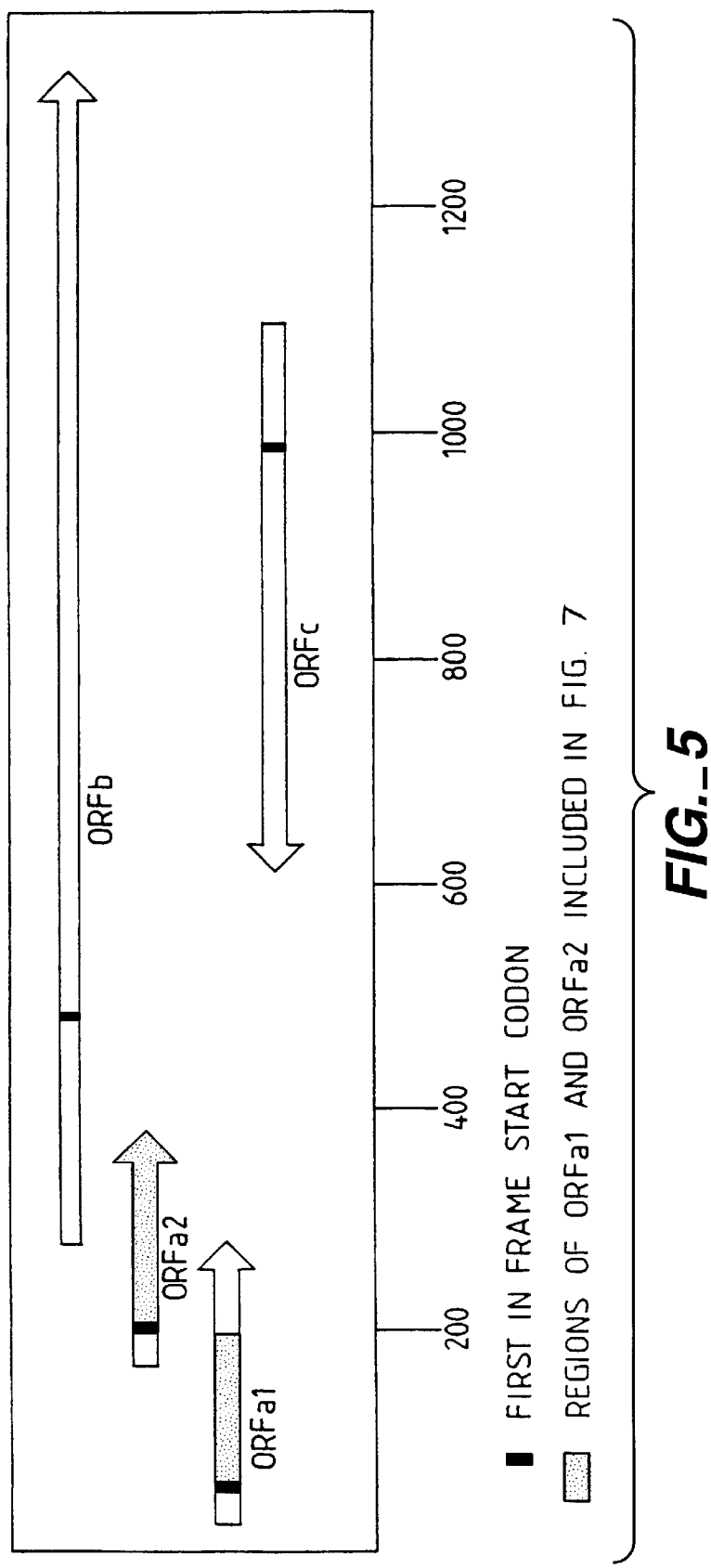
FIG._5

```
*   =>  match across all seqs.
.   =>  conservative substitutions
:   =>  IS986 (ORFb) matches 2 other sequences ORFb                                                    VPIAPSTYY---DHINREPSRRELRDGE---LKEHISRVH
IS3411   MMPLLDKLREQYGVGPLCSELHIAPSTYYH-CQQQRHHPDKRSARAQRDDWLKKQIQRVY
IS3      MKYV-FIEKHQAEFSIKAMCRVLRVARSGWYTWCQRRTRISTRQQFR----QHCDSVVLAAF
IS600                 MCQVFGVSRSGYYNWVQHEP--SDRKQSD-----ERLKLEIKVAH
                    .:.*:.:*       .       .....      ::      ::   .

ORFb     AANYGVYGARKVWLTLNREGIEVARCTV-ERLMTKLGLSGTTRGKARRTTIADPATARPADL
IS3411   DENHKVYGVRKVWRQLLREGIRVARCTV-ARLMAVMGLAGVLRGKKVRTTISRKAVA-AGHR
IS3      TRSKQRYGAPRLTDELRAQGYPFNVKTVAASLRRQ-GLRAKASRKFSPVSYRAHGLPVSENL
IS600    IRTRETYGTRRLQTELAENGIIVGRDRL-ARLRKELRLRCKQKRKFRATTNSNHNLPVAPNL
         **.:.:   *:  *: :*.**::*   .    *       :: .      .    :

ORFb     VQRRFGPPAPNRLWVADLTYVSTWAGFAYVAFVTDAYARRILGWRVASTMATSMVLDAIEQA
IS3411   VNRQFVAERPDQLWVADFTYVSTWRGFVYVAFIIDVFAGYIVGWRVSSSMETTFVLDALEQA
IS3      LEQDFYASGPNQKWAGDITYLRTDEGWLYLAVVIDLWSRAVIGWSMSPRMTAQLACDALQMA
IS600    LNQTFAPTAPNQVWVADLTYVATQEGWLYLAGIKDVYTCEIVRYAMGERMTKELTGKALFMA
          . .*  .   *:  *:..*:*.***:  *  *. *   :: *.:.     .:.  .*  *

ORFb     IWTRQQEGVLDLKDVIHHTDRGSQYTSIRFSERLAEAGIQPSVGAVGSSYDNALAETINGLY
IS3411   LWTRRPP
IS3411'           -GTVHHSDKGSQYVSLAYTQRLKEAGLLASTGSTGDSYDNAMAESINGLY
IS3      LWRRKRP------RNVIVHTDRGGQYCSADYQAQLKRHNLRGSMSAKGCCYDNACVESFFHSL
IS600    LRSQRPP------AGLIHHSDRGSQYCAYDYRVIQEQSGLKTSMSRKGNCYDNAPMESFWGTL
          :  :        . :::.*:*..**.:  .*:  :.     . .     ****  **.

ORFb     KTELIKPGKPWRSIEDVELATARWD-WFNHRRLYQYCGDVPPVELEAAYYAQRQRPAAG
IS3411'  KAEVIHR-KSWKNRAEVELATLTWD-WYNNRLLERLGHTPPAEAE
IS3      KVECIH-GEHFISREIMRATVFNYIECDYNRWRRHSWCGGLSPEQ----FENKNL--A
IS600    KNESLS-HYRFNNRDEAISVIREYIEIFYNRQRRHSRLGNISPAA----FREKYHQMAA
         * *  :              .     ..*  ..:* :.:  ..       .

FIG._6
```

```
*   =>  match across all relevant sequences
.   =>  conservative substitutions
:   =   IS986 (ORFa1 or ORFa2) matches 2 other sequences
```

```
ORFa1     MSGGSS------RRYPPELRERAVRMVAEIRGQHDSEWAAISEIARLLGV
ORFa2                                                            CAETVRKWVR
IS3411    MTKNT-------RFSPEVRQRAVRMVLESQSEYDSQWATICSIAPKIGCTRETLRVWVR
IS3       MTKTVSTSKKPRKQHSPEFRSEALKL------AERIGVTAAARELSLYESQLYNWRS
IS600     MSRKT-------QRYSKEFKAEAVRTVPENQ------LSISEGASRLSLPEGTLGQWVT
           *.          :  :*:.  *:::            .  :: .:  *:  .. *:

ORFa2     QAQVDAGARPGT-TTEESAEIKRLRRDNAELRRANAILKTASAFFA-AELDRP-AR
IS3411    QHERDTGGGDGGLTTAERQRLKELERENRELRRSNDILRQASAYFAKAEFDRLWKK
IS3       KQQNQQTSSEREL--EMSTEIARLKRQLAERDEELAILQKAATYFAK----RL-K
IS600     AARKGLGTPGSRTVAELESEILQLRKALNEARLERDILKKATAYFA-QES--L-KNTR
           .         :          *  :   **. *.*..*:. *** :.    :
```

FIG._7

```
IS986.IR_L       ccTGAACCGCCCCGGCATGTCC-GGAGACTC
IS986.IR_R       ccTGAACCGCCCCGGTGAGTCC-GGAGACTC
IS3411.IR_L         TGAACCGCCCCGG-GAATCCTGGAGACT
IS3411.IR_R         TGAACCGCCCCGG-GTTTCCTGGAGAGT
                    ********** ***  *** ***** *
```

\* = identical in all four sequences

FIG._8

```
* :=>   match across all seqs.
. :=>   conservative substitutions

5C      LTEL------------GVPIAPSTYY--DHINREPSRRELRDGE----LKEHISRVHA
IS3411  MMPLLDKLREQYGVGPLCSELHIAPSTYYHCQQQRHHPDKRSARAQRDDWLKKQIQRVYD
                        .:.*******    .  ....:..*. *.     **.* **..
        .       *

5C      ANYGVYGARKVWLTLNREGIEVARCTVERLMTKLGLSGTTRGKARRTTIADPATARPADL
IS3411  ENHKVYGVRKVWRQLLREGIRVARCTVARIMAVMGLAGVLRGKKVRTTISRKAVA-AGHR
        .*. ***.****  * ***** ******.***..*** **.. *** ****. *.* ...

5C      VQRRFGPPAPNRLWVADLTYVSTWAGFAYVAFVTDAYARRILGWRVASTMATSMVLDAIE
IS3411  VNRQFVAERPDQLWVADFTYVSTWRGFVYVAFIIDVFAGYIVGWRVSSSMETTFVLDALE
        *.*.*  . .*.*****:******.**.*****..*  ****:..*****..****.*

5C      QAIWTRQQEGVLDLKDVIHHTDRGSQYTSIRFSERLAEAGIQPSVGAVGSSYDNALAETI
IS3411  QALWTRRP------------------PARSITVIK------------VLSMYRWP---TH
        **.***..                  .:.   * *.            *   *      *

5C      NGLYKTELIKPGKPWRSIE-DVELATARWVDWFNHRRLYQYCGDVPPVELEAAYYAQRQR
IS3411  SGLRKPDY------wHQQEVQATRMTTRW-----RR-------------ASMVFTKRR-
        .** *.         :  . *.   :.. *     **              ..:. *.

5C      PAAG
IS3411  ----
```

FIG._9

```
*  :=> match across all seqs.
.  :=> conservative substitutions

5C   L-------TELGV--------PIAPSTYDHINREPSRRELRDGELKEHISRVHAANYG
IS3  MKYVFIEKHQAEFSIKAMCRVLRVARSGWYTWCQR-RTRISTRQ-QFRQHCDSVVLAAFT
     .         .          .:*.*..*.  .*  ..*.  ..*   *  ..* ..* *..

5C   V-----YGARKVWLTLNREGIEVARCTVERLMTKLGLSGTTRGKARRTTIADPATARPADL
IS3  RSKQRYGAPRLTDELRAQGYPFNVKTVAASLRRQGLRAKASRKFSPVSYRAHGLPVSENL
       *   *** .* *.  .*: .* * * ..*:..*.. *:*:.*:**:  : ::..    *

5C   VQRRFGPPAPNRLWVADLTYVSTWAGFAYVAFVTDAYARRILGWRVASTMATSMVLDAIE
IS3  LEQDFYASGPNQKWAGDITYLRTPEGWLYLAVVIDLWSRAVIGWSMSPRMTAQLACDALQ
     .:: *   .**::*.**:**: *  *: *.. * *  *: :*   * .  **. : **::

5C   QAIWTRQQEGVLDLKDVIHHTDRGSQYTSIRFSERLAEAGIQPSVGAVGSSYDNALAETI
IS3  MALWRRKRP-------RNVIVHTDRGGQYCSADYQAQLKRHNLRGSMSAKGCCYDNACVESF
     :*:**   .        :**:*****.**.* :.::*.:  ::.*..:*..****. *::

5C   NGLYKTELIKPGKPWRSIEDVELATARWVD-WFNHRRLYQYCGDVPPVELEAAYYAQRQR
IS3  FHSLKVECIH-GEHFISREIMRATVFNYIECDYNRWRRHSWCGGLSPEQFENKNLA----
       .*: *..*:  :.: *  ::  :: ..* *::: * : ..*** .** :* .:.

5C   PAAG
IS3  ----
```

FIG._10

```
*  :=>   match across all sequences.
.  :=>   conservative substitutions

IS3       MKYVFIEKHQAEFSIKAMCRVLRVARSGWYTWCQRRTRISTRQQFRQHCDSVVLAAFTRS
IS3411    MM-PLLDKLREQYGVGPLCSELHIAPSTYYH-CQQQRHHPDKRSARAQRDDWLKKQIQRV
5C        LT-EL--------------GVPIAPSTYY---DHINREPSRRE----LRDGELKEHISRV
                          .:.*:.*:.*           .  ..... :            *

IS3       KQR----YGAPRLTDELRAQGYPFNVKTVAASLRRQGLRAKASRKFSPVSYRAHGLPVSE
IS3411    YDENHKVYGVRKVWRQLLREGIRVARCTVARLMAVMGLAGVLRGKKVRTTISRKAVA-AG
5C        HAANYGVYGARKVWLILNREGIEVARCTVERLMTKLGLSGTTRGKARRTTIADPATARPA
             .     **..:..* .  :.**  **. *. ::*    * :  ::.:   : .

IS3       NLLEQDFYASGPNQKWAGDITYLRTPEGWLYLAVVIDLWSRAVIGWSMSPRMTAQLACDA
IS3411    HRVNRQFVAERPDQLWVADFTYVSTWRGFVYVAFIIDVFAGYIVGWRVSSSMETTFVLDA
5C        DLVQRRFGPPAPNRLWVADLTYVSTWAGFAYVAFVTDAYARRILGWRVASTMATSMVLDA
            ::..* :     : * *** **:  *..* : *.  *.:*  :** :  :  :: **

IS3       LQMALWRRKRP-------RNVIVHTDRGGQYCSADYQAQLKRHNLRGSMSAKGCCYDNACVE
IS3411    LEQALWTRRP--------PARSITVIK-------------VLSMYRWP-----
5C        IEQAIWTRQQEGVLDLKDVIHHTDRGSQYTSIRFSERLAEAGIQPSVGAVGSSYDNALAE
            .:* *    *                                      *

IS3       SFFHSLKVECIH-GEHFISREI-MRATVFNYIECDYNRWRRHSWCGGLSPEQFENKNLA-
IS3411    THSGLRKPDY-----WHQQEVQATRMTTRW------RR------ASMVFTK
5C        TINGLYKTELIKPGKPWRSIE-DVELATARWVD-WFNHRRLYQYCGDVPPVELEAAYYAQ
                  *                    :*       *                  .

IS3       ------
IS3411    RR----
5C        RQRPAAG
```

FIG._11

```
*  :=>  match across all seqs.
.  :=>  conservative substitutions

IS986
IS3411  MM-PLLDKLREQYGVGPLCSELHIAPSTYH-CQQQRHHPDKRSARAQRDDWLKKQIQRVYD
IS3     MKYVFIEKHQAEFSIKAMCRVLRVARSGWYTWCQRRTRISTRQQFRQHCD----SVVLAAFT
                                                 VPIAPSTYY---DHINREPSRRELRDGE---LKEHISRVHA
           .*.*..*           .     .      .    *

IS986    ANYGVYGARKVWLTLNREGIEVARCTVERLMTKLGLSGTTRGKARRTTIADPATARPADLVQ
IS3411   ENHKVYGVRKVWRQLLREGIRVARCTVARLMAVMGLAGVLRGKKVRTTISRKAVA-AGHRVN
IS3      RSKQRYGAPRLTDELRAQGYPFNVKTVAASLRRQGLRAKASRKFSPVSYRAHGLPVSENLIF
         **.....      *  .*     **       ** .                .

IS986    RRFGPPAPNRLWVADLTYVSTWAGFAYVAFVTDAYARRILGWRVASTMATSMVLDAIEQAIW
IS3411   RQFVAERPDQLWVADFTVVSTWRGFVVYVAFIIDVFAGYIVGWRVSSSMETTFVLDALEQALW
IS3      QDFYASGPNQKWAGDITYLRTPEGWLYLAVVIDLWSRAVIGWSMSPRMTAQLACDALQMALW
          .*   *..*..*....**.**       *   .  ..*      **      **..*.*

IS986    TRQQEGVLDLKDVIHHTDRGSQYTSIRFSERLAEAGIQPSVGAVGSSYDNALAETINGLYKI
IS3411   TRRPPA------RSITVIKVLSMYRWP-------THSGLRKP---------DYWHQQEV
IS3      RRKRP-------RNVIVHTDRGGQYCSADYQAQLKRHNLRGSMSAKGCCYDNACVESFFHSLKV
         *:.              .     :

IS986    ELIKPCKPWRSIEDVELATARWVD-WFNHRRLYQYCGDVPPVELEAAYYAQRQRPAAG
IS3411   QATRMTTRWRRASMV----------FTKRR-----------------------
IS3      ECIH-GEHFISREIMRATVFNYIECDYNRWRRHSWCGGLSPEQFENKNLA-----
              .....*
```

FIG._12

```
*   :=>  match across all seqs.
.   :=>  conservative substitutions

IS986                                                    VPIAPSTYY---DHINREPSRRELRDGE----LKEHISRVH
IS3411   MM-PLLDKLREQYGVGPLCSELHIAPSTYVH-CQQQRHHPDKRSARAQRDDWLKKQIQRVY
IS3      MKYVFIEKHQAEFSIKAMCRVLRVARSGWYTWCQRRTRISTRQQFRQHCD----SVVLAAF
                    .         .*.*...            *               .

IS986    AANYGVYGARKVWLTLNREGIEVARCTVERLMTKLGLSGTTRGKARRTTIADPATARPADL
IS3411   DENHKVYGVRKVWRQLLREGIRVARCTVARLMAVMGLAGVLRGKKVRTTISRKAVA-AGHR
IS3      TRSKQRYGAPRLTDELRAQGYPFNVKTVAASLRRQGLRAKASRKFSPVSYRAHGLPVSENL
             . **     .      **       . **        .    *            .

IS986    VQRRFGPPAPNRLWVADLTYVSTWAGFAYVAFVTDAYARRILGWRVASTMATSMVLDAIEQ
IS3411   VNRQFVAERPDQLWVADFTYVSTWRGFVYVVAFIIDVFAGYIVGWRVSSSMETTFVLDALEQ
IS3      LEQDFYASGPNQKWAGDITYLRTPEGWLYLAVVIDLWSRAVIGWSMSPRMTAQLACDALQM
            .       . *  * **. .   * .  *         *.*    .  **  ..

IS986    AIWTRQQEGVLDLKDVIHHTDRGSQYTSIRFSERLAEAGIQPSVGAVGSSYDNALAETING
IS3411   ALWTRRPPG       TVHHSDKGSQYVSLAYTQRLKEAGLLASTGSTGDSYDNAMAESING
IS3      ALWRRKRP------RNVIVHTDRGGQYCSADYQAQLKRHNLRGSMSAKGCCYDNACVESFFH
         *.* **               .    *.*.**  *    .**     *   ****  .*..

IS986    LYKTELIKPGKPWRSIEDVELATARWVD-WFNHRRLYQYCGDVPPVELEAAYYAQRQRPAA------
IS3411   LYKAEVIHR-KSWKNRAEVELATLTWVD-WYNNRRLLERLGHTPPAEAE--------
IS3 52   SLKVECIH-GEHFISREIMRATVFNYIECDYNRWRRHSWCCGLSPEQFENKNLA----
         *.*          ..   *   *  .*   .* ***
```

FIG._13

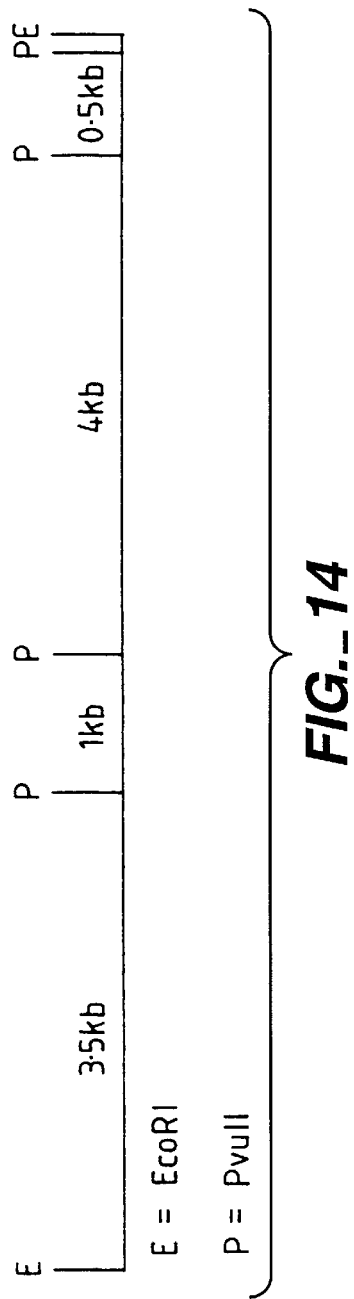
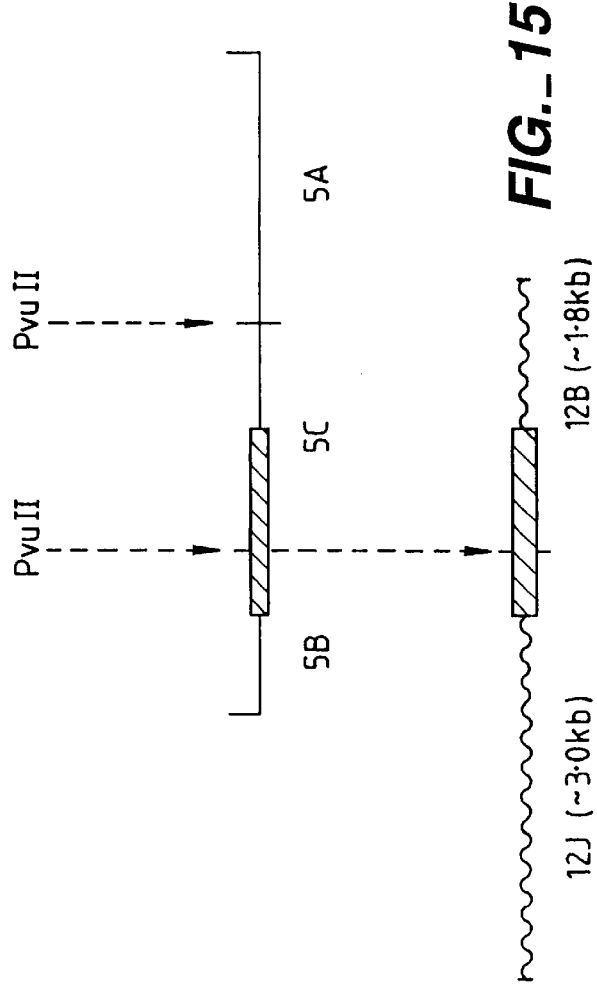
FIG._14
FIG._15

PROBES, KITS AND METHODS FOR THE DETECTION AND DIFFERENTIATION OF MYCOBACTERIA

This a continuation, of application Ser. No. 07/752,661 filed 18 Oct. 1991, now abandoned, and earlier international applications of record.

TECHNICAL FIELD

The present invention relates to gene probes, kits and methods for the detection and differentiation of Mycobacteria. In particular, the present invention relates to gene probes, kits and methods for the diagnosis of tuberculosis and/or for epidemiological study tools for investigating the progress of infections caused by members of the M.tuberculosis complex.

BACKGROUND ART

In some developed countries including the United Kingdom, tuberculosis is numerically one of the major notifiable infectious diseases and yet the mechanism of pathogenicity of M.tuberculosis is poorly understood. In the developing or 'third' world, this disease is an endemic health problem of vast proportions and therapy involves long periods of treatment with combinations of antibiotics. It is well recognized that one of the major problems in tackling tuberculosis is the lack of a simple, reliable and robust serodiagnostic or gene probe assay. These are necessary because current diagnostic tests, even those available in technically advanced rich nations, are poorly specific and insensitive, being based on a combination of relatively crude symptomology and radiography, staining for acid fast bacilli and bacterial culture. The first two are widely variable features and the second two are notoriously unreliable. In particular, with presently available tests, several weeks may be required to obtain a definite result and the detection of small numbers of M.tuberculosis bacteria in heavily contaminated samples is often difficult. The specific identification of Mycobacteria is also difficult, and especially the differentiation between the members of the M.tuberculosis complex: M.tuberculosis itself, the bovine strain M.bovis, M.africanum, M.microti and the vaccine strain BCG (which may cause disease in immunologically suppressed individuals. Many attempts have been made to develop new laboratory tests for tuberculosis but all have suffered from poor specificity and/or sensitivity. Gene probes for specific DNA sequences of the organism can detect small amounts of Mycobacterial genome reliably, by procedures that do not require a prolonged culture step or the laborious examination by trained staff of stained sputum smears. Gene probe analysis offers a sensitive method for the rapid detection of small numbers of specific bacteria in the presence of other organisms.

As well as being a significant health problem in humans, infections caused by Mycobacteria are also a significant health problem in cattle, deer, sheep and badgers and the probes provided herein are also useful for diagnostic/epidemiological study tools for use in respect of these species.

Gene probes for identifying strains of the M.tuberculosis complex are commercially available, but depend on detecting ribosomal RNA and require the bacteria to be cultivated first. Although these gene probes are capable of identifying the M.tuberculosis complex, they are not suitable for detecting bacteria in a specimen of sputum. The cultivation step also increases the test time and this is disadvantageous.

Described herein is the isolation and cloning of a fragment of M.tuberculosis DNA containing a repetitive element specific to the M.tuberculosis complex. This fragment hybridizes to multiple polymorphic restriction fragments in different isolates of M.tuberculosis and is therefore able to fingerprint isolates for studies of transmission of tuberculosis. Only a few hybridizing bands are detected in digests of M.bovis or BCG DNA, and the probe therefore has the unique ability to distinguish rapidly between these different members of the M.tuberculosis complex.

Several repetitive elements have been isolated from Mycobacterial species, including one from M.leprae (Clark-Curtiss, J. E. & Walsh, G. P. (1989) Journal of Bacteriology 171, 4844–4851; Clark-Curtiss, J. E. & Docherty, M. A. (1989) Journal of Infectious Diseases 159, 7–15; and Grosskinsky, C. M. Jacobs, W. R. Clark-Curtiss, J. E. & Bloom, B. R. (1989) Infection and Immunity 57, 1535–1541) and the insertion sequence IS900 from M.paratuberculosis (Green, E. P. Tizard, M. L. V. Moss, M. T. Thompson, J., Winterbourne, D. J., McFadden, J. J. & Hermon-Taylor, J. (1989) Nucleic Acids Research 17, 9063–9072). However, these repetitive elements are both species-specific and appear to give a constant hybridization pattern with strains from different sources.

This application describes the characterization and sequence analysis of a repetitive element, which identifies it as a member of the IS3 family of insertion sequences, of which several members have previously been characterized from species of the Enterobacteriaceae.

It has now been found that DNA probes having potential applications to the general diagnosis of Mycobacteria and to the specific diagnosis of tuberculosis can be derived from deoxyribonucleotide sequences capable of hybridizing with those sequences present in a naturally occurring plasmid.

As part of an investigation into antibiotic resistance, the presence of piasmids in M.tuberculosis was sought by hybridizing the total DNA from three clinical isolates with DNA from a naturally occurring plasmid known to exist in M.fortuitum (A. Labidi, C. Dauguet, K. S. Goh & H. L. David, 1984. Plasmid profiles of Mycobacterium fortuitum complex isolates. Current Microbiology 11: 235–240). Plasmids have not hitherto been found in M.tuberculosis, and it was hoped that they would be revealed by the use of the M.fortuitum plasmid DNA as a probe. Surprisingly, while this did not reveal the presence of any plasmids in M.tuberculosis, it did show that there are M.tuberculosis chromosomal DNA fragments which can hybridize with the plasmid DNA. Moreover, in total DNA from the three clinical isolates digested with restriction endonucleases BamHI or PvuII, the size of the hybridizing fragments was not the same for each strain.

Gene probes for the detection of Mycobacterial infection can have varying degrees of specificity depending on how unique the gene sequences they detect in a bacterial genome, are to a given family, genus, species or strain. Probes of different specificities can be of use depending on the clinical analysis required. Thus, one probe could detect a sequence pattern that is found in many different species (e.g; M.tuberculosis and M.bovis) within a given aenus (e.g; Mycobacterium). In other cases, gene probes may be specific for a particular species, and even or different strains of that species.

This varying specificity of gene probes has a practical use. For example, as a first line of diagnosis it may be more appropriate to use a probe which detected general Mycobacterial infection and then, if necessary use fine-tuning probes to diagnose which species of Mycobacteria are involved.

DISCLOSURE OF INVENTION

The present invention provides a nucleotide probe for the diagnosis and/or epidemiological study of Mycobacterial infection, which hybridizes with M.tuberculosis genomic DNA obtainable by screening a M.tuberculosis genomic library with DNA of a plasmid of M.fortuitum.

The present invention also provides a nucleotide probe for the diagnosis and/or epidemiological study of Mycobacterial infection, which hybridizes with genomic DNA of M.tuberculosis and with DNA of a plasmid of M.fortuitum.

The present invention also provides a nucleotide probe for the diagnosis and/or epidemiological study of Mycobacterial infection, which comprises, or hybridizes with, the nucleotide sequence (SEQ ID NO:1) depicted in FIG. 2 hereof or its complementary sequence, or which comprises or hybridizes with a nucleotide sequence obtainable from a genomic library of an organism of the M.tuberculosis complex, by hybridization with the nucleotide sequence (SEQ ID NO:1) depicted in FIG. 2 hereof, and which is capable of distinguishing and characterizing bacterial members of the M.tuberculosis complex either from each other, or from other bacteria not of the complex.

Also provided is a nucleotide probe for the diagnosis and/or epidemiological study of Mycobacterial infection, wherein the genomic library is obtainable from M.tuberculosis strain 50410.

The present invention also provides a nucleotide probe for the diagnosis and/or epidemiological study of Mycobacterial infection which comprises, or hybridizes with, part or all, of the nucleotide sequence shown in either FIG. 2 (SEQ ID NO:1) or FIG. 4 (SEQ ID NO:3) of the drawings or its complementary sequence.

The nucleotide probe may comprise or hybridize with part or all of an insertion element nucleotide sequence which in the genome of M.tuberculosis strain 50410 is bounded by two inverted repeat sequences and contains the nucleotide coding sequence identified in FIG. 2 (SEQ ID NO:1) of the drawings.

Also provided by the present invention is a nucleotide probe for the diagnosis and/or epidemiological study of Mycobacterial infection which comprises or hybridizes with a flanking sequence of nucleotides which in the genome of M.tuberculosis strain 50410 occur adjacent to an insertion element nucleotide sequence, bounded by two inverted repeat sequences and containing the nucleotide coding sequence identified in FIG. 2 (SEQ ID NO:1) of the drawings.

For example, the nucleotide probe may comprise or hybridize with part or all of the flanking sequence of nucleotides which occurs downstream of the 3' end of base 896 in FIG. 2 of the drawings.

The present invention also provides a nucleotide probe for the diagnosis and/or epidemiological study of Mycobacterial infection which comprises, or hybridizes with, part or all of an approximately 1.9 kb nucleotide sequence which, in the genome of M.tuberculosis strain 50410, occurs immediately downstream of the 3' end of the sequence shown in FIG. 2 of the drawings.

The present invention also provides a nucleotide probe for the diagnosis and/or epidemiological study of Mycobacterial infection, which comprises or hybridizes strongly with part or all of a nucleotide sequence which occurs in the genome of M.tuberculosis strain 50410 and which is characterised by the restriction map as shown in FIG. 1 of the drawings.

The nucleotide probe of the present invention may be used for the diagnosis of and/or epidemiological study of Mycobacterial infection. The nucleotide probes of the present invention may be able to distinguish between different strains of M.tuberculosis. The nucleotide probes of the present invention may be able to distinguish between M.tuberculosis, M.bovis and BCG. The nucleotide probes may not show significant hybridization with M.paratuberculosis, M.intracellulare, M.scrofulaceum, M.phlei, M.fortuitum, M.chelonei, M.kansasii, M.avium, M.malnioense, M.flavescens and M.gordonae.

The nucleotide probes of the present invention may be used for the detection of Mycobacteria in clinical samples by the techniques of dot blot analysis, solution hybridization, Southern blot analysis or polymerase chain reaction. The clinical samples may comprise sputum, urine, cerebrospinal fluid, tissue samples, blood and other body fluids.

The present invention also comprises diagnostic kits comprising the above described nucleotide probes.

The present invention also provides a method for detecting, distinguishing and/or characterizing Mycobacteria in clinical samples for the purposes of eoidemiological study which comprises using the above described nucleotide probes.

The present invention also provides methods for the production of said nucleotide probes.

The present invention also provides a method for distinguishing and characterizing bacterial members of the M.tuberculosis complex, both from each other and from other bacteria not of the complex, which method comprises: i) digesting DNA from a sample of bacteria with a particular restriction enzyme; and ii) carrying out hybridization analysis using an above described nucleotide probe.

The nucleotide sequence comprising the gene probe may not necessarily contain a restriction site for the restriction enzyme.

BRIEF DESCRIPTION OF DRAWINGS

In order that the present invention is more clearly understood, embodiments will be described in more detail by way of example only and with reference to the figures wherein:

FIG. 1 shows a restriction map of probe 5;

FIGS. 2A–B shows the DNA sequence (SEQ ID NO:1) of fragment 5C from probe 5 and the translation product of the large open reading frame (SEQ ID NO:2);

FIG. 3 shows a comparison of primary DNA structure of part of 5C compared with the insertion sequences IS3 and IS3411 of E.coli;

FIGS. 4A–B shows the DNA sequence (SEQ ID NO:3) overlapping part of fragment 5B and part of fragment 5C of probe 5, namely the insertion sequence (IS986) from the 5 kb DNA fragment of M. tuberculosis;

FIG. 5 shows the location of designated open reading frames;

FIG. 6 shows the alignment of potential translated product of IS986 ORFb (SEQ ID NO:4) with putative transposases of other IS3-like elements;

FIG. 7 shows the alignment of potential translated products of ORFa1 (SEQ ID NO:8) and ORFa2 (SEQ ID NO:9) with corresponding regions of other IS3-like elements;

FIG. 8 shows a comparison of the inverted repeat ends of ISTB (SEQ ID NO:13) and IS3411 (SEQ ID NO:14);

FIG. 9 shows the alignment of the potential translated products of the large open reading frames of 5C (SEQ ID NO:2) and IS3411 (SEQ ID NO:5);

FIG. 10 shows the alignment of the potential translated products of the large open reading frames of 5C and IS3 (SEQ ID NO:6);

FIG. 11 shows the alignment of the potential translated products of the large open reading frames of 5C (SEQ ID NO:2), IS3411 (SEQ ID NO:5) and IS3 (SEQ ID NO:6);

FIG. 12 shows the alignment of the potential translated products of the large open reading frames of the insertion sequence (IS986) (SEQ ID NO:4) from the 5 kb DNA fragment of M.tuberculosis with those of IS3411 (SEQ ID NO:5) and IS3 (SEQ ID NO:6);

FIG. 13 shows the alignment of the potential translated products of the large open reading frames of the insertion sequence (IS986) (SEQ ID NO:4) from the 5 kb DNA fragment of M.tuberculosis with those of IS3411 (SEQ ID NO:5) and IS3 (SEQ ID NO:6) wherein the C-terminal region of the IS3411 sequence (IS3411') (SEQ ID NO:15) is read from the −1 frame with respect to the rest of the IS3411 sequence;

FIG. 14 shows a restriction map of probe 9; and

FIG. 15 shows diagrammatically the relationship between probes 5 and 12J-B.

MODES FOR CARRYING OUT THE INVENTION

Probes 9 and 5

As part of an investigation into the possible presence of plasmids in clinical isolates of *M.tuberculosis*, total DNA from three such isolates was subjected to Southern blotting and probed with a naturally occurring plasmid from *M.fortuitum*. This plasmid, referred to as pUS300, was obtained from *M.fortuitum* strain CIPT 14-041-0003 in the Collection de I'Institut Pasteur, Tuberculose, Paris, France (deposited at the National Collection of Type Cultures, Colindale, London UK NW9 5HT under accession number NCTC 12381 on 21 Feb. 1990). The results showed that there were chromosomal DNA fragments in the strains of *M.tuberculosis* which were capable of hybridizing to this *M.fortuitum* plasmid, and also that in material digested with BamHI or PvuII, the sizes of the hybridizing fragments were not the same for each strain.

In order to isolate these hybridizing fragments, a total DNA library from a clinical isolate of *M.tuberculosis* (strain 50410, obtained from the Public Health Laboratory, Dulwich, London, England) was constructed in the lambda phage vector EMBL4 by ligation of a partial Sau3AI digest of the *M.tuberculosis* DNA with BamHI-digested EMBL4. The library was screened with a DNA probe derived by labelling a recombinant plasmid pUS301. This plasmid was constructed by ligating an EcoRI digest of plasmid pUS300 with an EcoRI digest of the *E.coli* plasmid vector pUC19. Positive plaques were purified through further rounds of plaque screening. The probes described below are obtained from the recombinant phage, referred to as the EMBL4/A-3 clone (deposited at the National Collection of Type Culture, Colindale, London UK NW9 5HT under accession number NCTC 12380 on 21 Feb. 1990), of one of the positive plaques obtained by this procedure.

The DNA from this recombinant phage EMBL4/A-3 clone was extracted and digested with EcoRI. Agarose gel electrophoresis and Southern blotting demonstrated that EcoRI-digested EMBL4/A-3 contained a series of fragments including one of approximate size 9000 base pairs (9 kb) and one of approximate size 5000 base pairs (5 kb) which hybridized with the plasmid pUS300. These fragments were each excised from the gel and are referred to as probe 9 (the 9 kb fragment) and probe 5 (the 5 kb fragment) respectively.

Isolation of the probe 5 by hybridization with *M.fortuitum* plasmid pUS300 is more fully described in Zainuddin and Dale; J. Gen. Micro. (1989) 135, pp 2347–2355.

The 5 kb EcoRI fragment from the lambda clone A3 (Zainuddin, Z. F. & Dale, J. W. (1989) Journal of General Microbiology 135, 2347–2355) was cloned using the plasmid vector pAT153 to generate plasmid pRP5000. Digestion of the insert fragment from pRP5000 with PvuII generated three fragments designated 5A, 5B and 5C (FIG. 1) which were converted to blunt-ended fragments and ligated with PvuII digested pAT153, generating plasmids pRP5100, pRP5200 and pRP5300 respectively.

Specific subfragments from pRP5000, pRP5200 and pRP5300 generated using BamHI, XhoI, HindIII and SalI (FIG. 1) were cloned in M13mp18 and M13mp19 using the M13 Cloning Kit (New England Biolabs). The smaller EcoRI-BamHI fragment from pRP5000 was cloned into Bluescript pKS and nested deletions were carried out using the Erase-a-Base technique (Promega). Seauencing was performed with Taq and T7 polymerases (Promega) and Sequenase Version 2 (US Biochemicals), using the 370 Automated Sequencer (Applied Biosystems). Fragments with overlaps of at least 50 bp were sequenced in both directions.

Searches of GenBank, EMBL, NBRF and SwissProt databanks were carried out using the SEQNET node at the SERC facility at Daresbury, by means of the UWGCG package and WordSearch program (Devereux, J., Haeberli, P. & Smithies, O. (1984) Nucleic Acids Research 12, 387–395; and Wilbur, W. J. & Lipman, D. J. (1983) Proceedings of the National Academy of Sciences USA 80, 726–730) and the NAQ program from the Protein Identification Resource. Sequence analyses were performed with the Staden-Plus package (Amersham) using DIAGON (Staden, R. (1982) Nucleic Acids Research 10, 2951–2961) for sequence comparisons and both Positional Base Preference (Staden, R. (1984) Nucleic Acids Research 12, 551–567) and Shepherd RNY (Shepherd, J. C. W. (1981) Proceedings of the National Academy of Sciences USA 78, 1596–1600) methods for identification of reading frames, supplemented by the use of codon preference analysis (Staden, R. & McLachlan, A. D. (1982) Nucleic Acids Research 10, 141–156) based on a table of preferred codon usage in *M.tuberculosis* (Dale, J. W. and Patki, A. (1990) in The Molecular Biology of Mycobacteria (McFadden, J. J. Ed.) in press). Multiple sequence alignments were carried out with the CLUSTAL software (Higgins, D. G. & Sharp, P. M. (1988) Gene 73, 237–244) supplemented by manual adjustment.

Probe 9

Probe 9 was radioactively labelled with $^{32}P$ using the Multiprime Random Primer Extension method (Amersham) and hybridized to Southern blots of PvuII-digested total DNA from eight clinical isolates of *M.tuberculosis* (isolate numbers 50410, 60925, 61066, 61104, 61125, 61267, 61377, 61513) as well as *M.bovis* (field strain, Central Veterinary Laboratory) and BCG (NCTC 5692). After agarose gel electrophoresis, the DNA fragments were transferred to a Hybond-N filter and fixed by baking at 80° C. for 1 hour. The filter was prehybridized at 68° C. in hybridization buffer. Hybridization with the probe was carried out in the same buffer at 68° C. overnight.

The hybridization buffer consisted of 5× Denhardt's solution, 5× SSPE buffer, 0.2% sodium dodecyl suiphate (SDS) and 100 μg./ml. sonicated salmon sperm DNA. The Denhardt's solution and the SSPE buffer were made up as stock solutions as follows:

50× Denhardt's solution: 0.5 g. Ficoll (mw 400,000), 0.5 g. polyvinylpyrrolidone (mw 40,000), 0.5 g. bovine serum albumin, were dissolved in sterile deionized distilled water to a final volume of 50 mls which was dispensed into aliquots and stored at −20° C.

20× SSPE buffer: 3.6M NaCl, 20 mM ethylenediaminetetra-acetic acid (EDTA), 0.2M $NaH_2PO_4$/$Na_2HPO_4$, pH 7.7 were dissolved in deionized distilled water and autoclaved.

The filter was then washed twice with 2× SSC, once with 2× SSC containing 0.1% SDS and once with 0.1× SSC containing 0.1% SDS. All washes were done at 68° C. The SSC was made up as a stock solution as follows:

20× SSC: 3M NaCl, 0.3M sodium citrate were dissolved in distilled water and autoclaved after the pH had been adjusted to 7.0.

The filter was covered with Saran wrap and exposed to X-ray film (RX, Fuji) for 16 hours at room temperature.

Each strain of *M.tuberculosis* hybridized to probe 9 exhibited several hybridizing bands; some elements of this pattern varied from strain to strain while others remained constant. *M.bovis* and BCG also hybridized to probe 9 with a pattern which retained the conserved features of the *M.tuberculosis* pattern.

The following species of Mycobacteria (one strain each except where indicated) did not hybridize with probe 9 to any significant extent: *M.paratuberculosis*, *M.intracellulare*, *M.scrofulaceum*, *M.phlei*, *M.fortuitum* (three strains), *M.kansasii*, *M.avium*, *M.malnioense*, *M.flavescens*, *M.gordonae* and *M.chelonei* (two strains).

Probe 9 was, therefore, specific for the *M.tuberculosis* complex (which includes *M.bovis* and BCG), with some ability to differentiate between strains.

A restriction map of probe 9 is shown in FIG. 14. The probe is bound by two EcoRI sites and divided by four internal PvuII sites into fragments of approximately 3.5 kb, 1 kb, 4 kb and 0.5 kb.

Probe 5

Studies on probe 5 have revealed that it comprises a sequence which encodes an insertion element (designated IS986) which appears to be present in a variable number of copies (up to about 15) in *M.tuberculosis*, *M.bovis*, *M.africanum*, *M.microti* and *M.bovis* BCG of the *M.tuberculosis* complex. The insertion element has been compared to the previously described insertion elements IS 3 and IS 3411 found in *E.coli*. The insertion element of probe 5 has close homology to IS 3411 which probably encodes a transposase.

A restriction map of probe 5 is shown in FIG. 1. The probe can be divided at two PvuII sites into fragments 5A, 5B and 5C (SEQ ID NO: 1) as shown.

The sequence of 5C is shown in FIG. 2. Useful restriction sites are boxed and a sequence with 29/40 identity with the right-hand inverted repeat (IR) from IS 3411 and 20/40 with the inverted repeat from IS 3 is overlined (Ishiguro & Sato 1988, J. Bacteriology 170, 1902–1906; Timmerman & Yu 1985, Nucl. Acids Res. 13, 2127–2139). Line diagrams comparing the primary DNA structure of part of 5C compared with IS 3 and IS 3411 are shown in FIG. 3.

FIG. 4 shows a DNA sequence (SEQ ID NO: 3) which overlaps part of fragment 5B and part of fragment 5C of probe 5. As in FIG. 2 useful restriction sites are boxed. The PvuII restriction site defines the join between fragments 5B and 5C. This DNA sequence comprises two inverted repeat sequences (27/30 bases matching) which have been underlined in FIG. 4. The left-hand inverted repeat CCTGAAC-CGCCCCGG CATGTCCGGAGACTC is located within fragment 5B to the 5' side of a first Acc III site, whilst the right-hand inverted repeat GAGTCTCCGGACTCAC-CGGGGCGGTTCAGG is located within fragment 5C to the 3' side of a second Acc III site. The sequence between these inverted repeat sequences comprises the insertion element IS986 (of approximately 1358 bp) which is present in a variable number of copies in members of the *M.tuberculosis* complex.

Examination of the insertion element revealed one long open reading frame (ORFb: bases 274 to 1311) (SEQ ID NO:4) with a potential translational start codon (GUG) at position 478, and another (ORFc) in the reverse direction (1107 to 622) (FIG. 5). Positional base preference analyses indicated both of these as potentially translated regions, together with parts of two shorter ORFs (6 to 275 and 164 to 376). (For reasons discussed below, the latter two are considered together and designated ORFa1 (SEQ ID NO:8) and ORFa2 (SEQ ID NO:9) respectively; the regions likely to be translated are indicated in FIG. 5. The codon usage of ORFb, and to a lesser extent ORFc, is consistent with the high degree of codon bias normally shown by mycobacterial genes (Dale, J. W. and Patki, A. (1990) in The Molecular Biology of Mycobacteria (McFadden, J. J., Ed.) in press). This was also true of the indicated regions of ORFa1 and ORFa2 (FIG. 5), although not for the remainder of these ORFs (see below)).

The sequence of the hypothetical translation product of ORFb (SEQ ID NO:4) was screened against the NBRF and SwissProt databanks. One sequence was identified with homology significantly above background, which was the putative transposase protein or the insertion sequence IS3411, (SEQ ID NO:5) from *E.coli* (Ishiguro and Sato; 1988, J. Bacteriology 170, 1902–1906); a lower degree of similarity was seen with hypothetical proteins translated from the sequences of two other insertion sequences, IS600 (SEQ ID NO:7) and IS629, both from *Shigella sonnei* (Matsutani, S., Ohtsubo, H., Maeda, Y. & Ohtsubo, E. (1987) Journal of Molecular Biology 196, 445–455). All these sequences belong to the IS3 family.

A multiple alignment of these sequences, and that of the IS3 transposase (Timmerman, K. P. & Tu, C-P. D. (1985) Nucleic Acids Research 13, 2127–2139), demonstrates a marked degree of resemblance except for the C-terminal oortion of the IS3411 protein. The different structure of this region of IS3411 is also evident from the alignment of the putative transposases (proteins which allow the DNA segment comprising the insertion element bound by inverted repeats, to excise and insert at another part of the genome), of IS3 and IS3411 as shown by Ishiguro & Sato 1988. However, a comparison of the products of all three reading frames of the complete sequences of IS3 (SEQ ID NO:6), IS3411 (SEQ ID NO:5) and IS986 (SEQ ID NO:4) showed homology of the C-terminal portion of the IS986 ORFb with the −1 frame of IS3411 (SEQ ID NO:15). A multiple alignment, using an IS3411 product with a hypothetical frameshift (FIG. 6) (the sequences were split at the point corresponding to the putative frameshift in IS3411; the two portions were aligned separately and re-combined manually. IS3411' (SEQ ID NO:15) is read from the −1 frame with respect to the first part of the sequence), shows that 27% of the amino acid residues of the IS986 ORFb (SEQ ID NO:4) product are also present n at least two of the other three sequences used for comparison, with about half of these being identical in all four sequences. Clusters of identical residues can be seen in three regions containing the conserved motifs L/VWV/AADLTYV, IHHT/SDRGSQY and C/SYDNA. The degree of conservation of these regions suggests that they are essential for the function of this protein.

The sequence prior to the potential start codon in ORFb (GUG$_{478}$) bears only a weak resemblance to a consensus Shine-Dalgarno sequence, which is probably not significant. Therefore the nature of the potential translation start of ORFb was investigated by examination of the upstream region. The three-frame comparison of the translation products of IS3, IS3411 (SEQ ID NO:5) and IS986 (SEQ ID NO:4) indicated further similarities in this region. In both IS3 and IS3411, the putative transposase gene (ORFb) is preceded by an open reading frame of about 300 base pairs, with good translational start signals (Ishiguro, N. & Sato, G. (1988) Journal of Bacteriology 170, 1902–1906; and Matsutani, S., Ohtsubo, H., Maeda, Y. & Ohtsubo, E. (1987) Journal of Molecular Biology 196, 445–455). The hypothetical products of the relevant regions of these ORFs align well with those of ORFa1 (SEQ ID NO:8) and ORFa2 (SEQ ID NO:9) (FIG. 7) (the translated products of ORFa1 (SEQ ID NO:8) and ORFa2 (SEQ ID NO:9), up to and starting from the position of the suggested frameshift, were aligned with the products of the corresponding reading frame of the other elements. All sequences shown, except ORFa2, started from the presumed AUG initiation codon) indicating a possible frameshift in the IS986 sequence. Alternatively, there is a potential start codon (GUG$_{200}$) five amino acids into the sequence shown in FIG. 7; so it is conceivable that ORFa2 is translated independently. The potential ribosome binding site indicated in FIG. 7 is only separated from the GUG codon by a single base and is therefore of doubtful significance. Of the combined ORFa1 (SEQ ID NO:8) and ORFa2 (SEQ ID NO:9) products, 29% of residues are found in two of the other three sequences shown. Pairwise comparisons confirm the alignments; for example, 50% of the residues match with the IS3411 ORFa product. The alignment shown in FIG. 7 is in marked contrast to the finding of Schwartz et al (Schwartz, E., Kroger, M. & Rak, B. (1988) Nucleic Acids Research 13, 2127–2139) that the ORFa products of several elements of the IS3 family showed only marginal homology.

The IS986 ORFa1 (SEQ ID NO:8) has a potential initiation codon (AUG) at position 54, preceded by a purine-rich region with several possible assignments of sequences showing five out of seven bases matching the consensus Shine-Dalgarno sequence. With several other members of the IS3 family, translation of the putative transposase (ORFb) is thought to occur by readthrough from ORFa. In both IS3411 (SEQ ID NO:10) and IS3 (SEQ ID NO:11), the translational stop signal ending ORFa overlaps the putative start codon for ORFb, with the sequence AUGA. A ribosome terminating at this point could therefore reinitiate at the overlapping AUG codon. However, in IS986, although ORFa2 overlaps ORFb, there is no potential start codon in the overlapping region of ORFb.

Ribosomal frameshifting, generating a fusion protein, has been shown to occur in IS1 (Sekine, Y. & Ohtsubo, E. (1989) Proceedings of the National Academy of Sciences USA 86, 4609–4613) in a region where two ORFs overlap, probably at the sequence UUUAAAAAC. IS3411, IS3 and IS600 all contain runs of 5–7 A residues in the overlap region between the two ORFs. The overlap region between ORFa2 and ORFb in IS986 does not contain such a long run of adenines, but the sequence UUUUAAAG (324–331) may be a candidate for such a frameshifting event. Translational frameshifting in the −1 direction also occurs in other prokaryotic genes which do not appear to possess a common sequence (Atkins, J. F. Gesteland, R. F., Reid, B. R. & Anderson, C. W. (1979) Cell 18, 1119–1131).

The significance of ORFC, on the reverse strand, is unclear. The first potential start codon (AUG$_{1002}$) is not preceded by anything resembling a Shine-Dalgarno sequence. Although analysis of ORFC is consistent with it being a translated sequence, it is in register with ORFb on the other strand, and the analytical procedures on the two strands are not independent. Schwartz et al (Schwartz, E., Kroger, M. & Rak, B. (1988) Nucleic Acids Research 14, 6789–6802) have identified a similar ORF in the E.coli element IS150, which appears to have a coding function. The presence of ORFs on the reverse strand is a common feature of other IS elements, and is considered to be involved in the regulation of transposition possibly by the requirement for both proteins ensuring that the IS element cannot be gratuitously activated by external transcription (Galas, D. J. and Chandler, M. (1989) in Mobile DNA (Berg, D. E. and Howe, M. M., Eds.), pp. 109–162, American Society for Microbiology, Washington). Further work is required to define the actual nature of the translational (and transcriptional) control signals operating in M. tuberculosis.

The base composition of IS986 is typical of M.tuberculosis, at 64% G+C. It is therefore not surprising that the homology with the other members of the IS3 family, which is so pronounced at the protein level, is much less striking at the DNA level (data not shown). There is however a marked degree of similarity of the inverted repeat ends with the other members of the IS3 family, especially IS3411 (SEQ ID NO:14) (FIG. 8) where the IR ends are 78% identical to those of IS986 (SEQ ID NO:13).

FIG. 9 shows that the translation of the large open reading frame from 5C (SEQ ID NO:2) is strongly homologous to the large open reading frame of insertion element IS3411 (SEQ ID NO:5) from E.coli. It is also homologous to IS3 from E.coli (FIG. 10). The alignment of all three sequences is shown in FIG. 11.

The alignment of the potential translated products of the large open reading frames of the insertion sequence from the 5 kb DNA fragment of M.tuberculosis (IS986) (SEQ ID NO:4) with those of IS3411 (SEQ ID NO:5) and IS3 (SEQ ID NO:6) is shown in FIG. 12. In FIG. 13 a similar comparison is made, but here the C-terminal region of the IS3411 sequence (IS3411') (SEQ ID NO:15) is read from the −1 frame with respect to the rest of the IS3411 sequence.

Probe 5 was tested by hybridization experiments substantially as described for probe 9 with 22 isolates of M.tuberculosis as well as M.bovis and BCG. The conditions were the same as described above for probe 9, except that autoradiography was for 6.5 hours at room temperature.

Each M.tuberculosis strain showed between five and fifteen strongly hybridizing fragments, as well as a number of weaker bands. The number of bands and the strength of the signal, as well as the variation between strains, indicated the presence of a randomly inserted repetitive DNA element in the chromosome of these strains.

M.bovis and BCG showed a simpler pattern of two and three major bands respectively. These organisms could therefore be easily distinguished from M.tuberculosis and from each other.

The following species of mycobacteria (one strain each except where indicated) did not hybridize with probe 5: M.paratuberculosis, M.intracellulare, M.scrofulaceum, M.phlei, M.fortuitum (three strains), M.kansasii, M.avium, M.malnioense, M.flavescens, M.gordonae and M.chelonei (two strains).

Probe 5 was, therefore, specific for the M.tuberculosis complex and was in addition able to distinguish between M.tuberculosis, M.bovis and BCG, and to distinguish between strains of M.tuberculosis.

Fragment 5A on Southern blot, hybridizes strongly and specifically with DNA from M.tuberculosis H$_{37}$Rv and H$_{37}$Ra, and M.bovis BCG giving identical bands in each, of size 2.1 and 0.65 kbp, although it does not necessarily give these sized bands with any strain of M.tuberculosis.

INDUSTRIAL APPLICABILITY

Part or all of the sequences identified and which comprise part or all of probe 5 can be used as gene probes. In particular, part or all of the sequences identified in 5C and 5B, as constituting the insertion element can be used as gene probes. When such probes are used in hybridization studies on cleaved genomic DNA from bacterial specimens of the M.tuberculosis complex, characteristic banding patterns are produced and therefore such probes are useful as diagnostic and epidemiological tools. Not only different species, but different strains within a species produce characteristic banding patterns. This is particularly useful for distinguishing M.bovis and M.bovis BCG from other species, and indeed M.bovis from M.bovis BCG. Probe 5A could be used as a generic probe, for detecting all members of the M.tuberculosis complex.

The usefulness of probe 5 or a fragment thereof as a diagnostic tool is largely due to the following features.

a) The insertion element has only been found in members of the M.tuberculosis complex (M.tuberculosis, M.bovis, M.africanum and M.microti) and not in nonpathogenic environmental Mycobacteria nor M.leprae.

b) Using Southern blot analysis with probe 5 (or a part of the insertion element in 5) as a probe, a different pattern of bands is seen with each M.tuberculosis isolate tested (22 to date). This would be a powerful tool in epidemiological studies to examine tuberculosis transmission.

c) It is one of the first probes to show differences between M.tuberculosis and M.bovis and perhaps more importantly between M.bovis and M.bovis BCG.

d) The use of the insertion element as a probe to distinguish M.bovis BCG from M.bovis and M.tuberculosis is useful in patients with disseminated BCG infection following vaccination or immunosuppression.

e) Insertion elements (flanked by two insertion sequences) are useful genetic tools in characterizing unknown genes.

Thus, the present invention provides a number of ways of distinguishing and characterizing bacterial members of the M.tuberculosis complex, both from each other and from other bacteria not of the complex.

For example, DNA from a sample of bacteria can be digested with a particular restriction enzyme and a hybridization analysis carried out (in accordance with standard techniques) using as a probe a fragment of the DNA disclosed herein, which fragment does not contain the restriction site used to cleave the sample DNA. For example, a BamHI to Xho I fragment (or a part thereof) of probe 5/5C (see FIG. 1 and bases 420 to 810 of FIG. 2) which is located within the insertion element and which does not contain any PvuII sites, was used to probe a PvuII digest of M.bovis BCG DNA. roughen this was done, strong hybridization to a single band was observed, indicating that in the M.bovis BCG strain tested, the insertion element is present in a single copy.

Employing a probe which contains the restriction site used to cleave the sample DNA, will give rise to multiple band hybridization, as will also occur if the sample DNA contains multiple copies of e.g. the insertion element; as appears to be the case with most members of the M.tuberculosis complex. Nevertheless, the banding hybridisation patterns can be used to distinguish between different strains of the same species, and between different species of the M.tuberculosis complex. A generic probe for detecting all members of the M.tuberculosis complex need not include DNA from the insertion sequence, but could be exclusively from the flanking DNA, such as PvuII-EcoRI fragment 5A, as discussed above.

The existence in M.tuberculosis of an insertion sequence so closely related to characterized IS elements from the Enterobacteriaceae is of considerable significance from several points of view. The multiple restriction fragment length polymorphisms detected (Zainuddin, Z. F. & Dale, J. W. (1989) Journal of General Microbiology 135, 2347–2355) indicate that a number of copies of IS986 are inserted at different sites in different isolates of M.tuberculosis. In this respect it differs from other recently described repetitive elements from mycobacteria (Clark-Curtiss, J. E. & Walsh, G. P. (1989) Journal of Bacteriology 171, 4844–4851; Clark-Curtiss, J. E. & Docherty, M. A. (1989) Journal of Infectious Diseases 159, 7–15; and Green, E. P., Tizard, M. L. V., Moss, M. T., Thompson, J., Winterbourne, D. J., McFadden, J. J. & Hermon-Taylor, J. (1989) Nucleic Acids Research 17, 9063–9072) which give identical Southern blot patterns with different isolates. This suggests that IS986 may be a functional transposable element in mycobacteria, which would be of considerable value for transposon mutagenesis of mycobacterial species. The transposability of IS986 may be regulated by ribosomal frameshifting in the overlap between ORFa and ORFb, as has been established for IS1 (Sekine, Y. & Ohtsubo, E. (1989) Proceedings of the National Academy of Sciences USA 86, 4609–4613).

The presence of IS986 in clinically isolated strains of M.tuberculosis from a wide variety of sources (Zainuddin, Z. F. & Dale, J. W. (1989) Journal of General Microbiology 135, 2347–2355) and the relationship with the IS elements from E.coli and Sh.sonnei, suggest the possibility of transfer of genetic material amongst M.tuberculosis strains as well as acquisition from Gram negative bacteria. It has been suggested (Zainuddin, Z. F. & Dale, J. W. (1990) Tubercle 71, in press) that at least some clinical strains of M.tuberculosis carry plasmids, and these may play a role in the dissemination of such elements; the ability of some E.coli plasmids to replicate in Mycobacteria (Zainuddin, Z., Kunze, Z. & Dale, J. W. (1989) Molecular Microbiology, 29–34) may have enabled insertion sequences to spread from E.coli to M.tuberculosis. However, conjugation has never been conclusively demonstrated in M.tuberculosis, and the organism normally has a solitary existence, apart from incidental encounters with other organisms, e.g., in the gut. Therefore, transmission of plasmids carrying insertion sequences would probably be a rare event. The high G+C composition of the IS element indicates that its acquisition by M.tuberculosis is not a recent event. These questions may be resolved by a study of the behavior of this insertion sequence in laboratory strains and clinical isolates.

IS986 is found in all species of the M.tuberculosis complex, although the copy number varies, and is not found in other mycobacterial species (Zainuddin, Z. F. & Dale, J. W. (1989) Journal of General Microbiology 135, 2347–2355). Therefore, probes based on IS986 will be highly specific for pathogenic mycobacteria. Coupled with the use of the Polymerase Chain Reaction (PCR), this will provide an exceptionally sensitive system for the detection and speciation of M.tuberculosis in clinical specimens. The extensive polymorphism of M.tuberculosis isolates testes with this probe (Zainuddin, Z. F. & Dale, J. W. (1989) Journal of General Microbiology 135, 2347–2355) enables extremely precise epidemiological investigations to be carried out, by fingerprinting clinical isolates. With this system all but the most closely related isolates will yield different patterns of hybridizing restriction fragments, and it will thus be possible to track the spread of different strains of *M.tuberculosis* through a community.

Probe 12

"Probe 12" is an Eco RI fragment of around 25.2 Kb from *M.tuberculosis* NCTC 7416 $H_{37}Rv$, obtained by screening a library of EcoRI—digested $H_{37}Rv$ under stringent conditions, with $H_{37}Rv$ DNA and isolating a strongly hybridizing clone.

The 25.2 kb EcoRI fragment is digested by PvuII into fragments of approximate size 8.9 kb, 3.8 kb, 3.5 kb, 3.0 kb (fragment 12J), 1.8 kb (fragment 12B), 1.6 kb, 1.4 kb, and 1.2 kb (fragment 12A). The 1.2 kb 12A fragment is *M.tuberculosis* complex specific and not related to probes 5 or 9. FIG. 15 shows the arrangement of the 12J and 12B fragments with respect to probe 5. The DNA flanking the insertion sequence is illustrated by a wavy line as it is not identical to the flanking DNA in probe 5, owing to the fact that the insertion element inserts at many places in the genome. The flanking DNA of probe 12J hybridizes with many different species of Mycobacteria. Fragment 12J could have value as a diagnostic probe for detecting a wide range of Mycobacteria.

Probe 8

This describes an Eco RV fragment of approximately 16.1 kb isolated by hybridization screening on Eco RV library of $H_{37}Rv$.

When used as a probe on a Southern blot with DNA from *M.tuberculosis* it binds to many fragments. On PvuII digestion it yields fragments of approximate size 5.6 kb, 4.8 kb, 2.1 kb, 2.0 kb, 0.9 kb and 0.7 kb. It does not appear to be related to probes 5 and 12.

---

We claim:

1. A nucleotide probe for the diagnosis and/or epidemiological study of Mycobacterial infection that specifically hybridizes to nucleic acid from members of the *Mycobacterium tuberculosis* complex but not to nucleic acid from mycobacteria that are not members of the complex, wherein said nucleotide probe comprises, or hybridizes with, *Mycobacterium tuberculosis* DNA from recombinant phage EMBL4/A-3 (accession number NCTC 12380).

2. A nucleotide probe according to claim 1 wherein said DNA from recombinant phage EMBL4/A-3 comprises a nucleotide sequence depicted in FIG. 2 (SEQ ID NO:1) of the drawings, or its complementary sequence.

3. A nucleotide probe according to claim 1 wherein said DNA from recombinant phage EMBL4/A-3 comprises an approximately 5 kb fragment of an EcoR1 digest of said recombinant phage EMBL4/A-3, or its complementary sequence.

4. A nucleotide probe according to claim 1 wherein said DNA from recombinant phage EMBL4/A-3 comprises a nucleotide sequence depicted in FIG. 4 (SEQ ID NO:3) of the drawings, or its complementary sequence.

5. A nucleotide probe according to claim 1 wherein said DNA comprises an approximately 9 kb fragment of an EcoR1 digest of said recombinant phage EMBL4/A-3, or its complementary sequence.

6. A nucleotide probe according to claim 1 which comprises, or hybridizes with, a flanking sequence of nucleotides which, in the genome of *Mycobacterium tuberculosis* strain 50410, occur adjacent to an insertion element nucleotide sequence bounded by two inverted repeat sequences and containing the nucleotide coding sequence identified in FIG. 2 (SEQ ID NO:1) of the drawings.

7. A nucleotide probe according to claim 6 which comprises, or hybridizes with, a sequence of nucleotides which occurs downstream of the 3' end of base 896 in FIG. 2 (SEQ ID NO:1) of the drawings, or its complementary sequence.

8. A nucleotide probe for the diagnosis and/or epidemiological study of Mycobacterial infection that specifically hybridizes to nucleic acid from members of the *M. tuberculosis* complex but not to nucleic acid from mycobacteria that are not members of the complex, wherein said nucleotide probe comprises, or specifically hybridizes under stringent conditions with an approximately 1.9 kb nucleotide sequence which sequence, in the genome of *Mycobacterium tuberculosis* strain 50410, occurs downstream of the 3' end of the nucleotide sequence shown in FIG. 2 (SEQ ID NO:1) of the drawings, as depicted as fragment 5A in FIG. 1 of the drawings, or its complementary strand thereof.

9. A nucleotide probe according to claim 1 which can distinguish between *Mycobacterium tuberculosis, Mycobacterium bovis* and BCG.

10. A nucleotide probe according to claim 1 which can distinguish between different strains or isolates of *Mycobacterium tuberculosis*.

11. A method for detecting, distinguishing and/or characterizing Mycobacteria in clinical samples for the purposes of epidemiological study which comprises using a nucleotide probe according to claim 1.

12. A method for distinguishing and characterizing bacterial members of the *Mycobacterium tuberculosis* complex, either from each other, or from other bacteria not of the complex which comprises:

digesting DNA from a sample of bacteria with a particular restriction enzyme; and carrying out hybridization analysis using a nucleotide probe according to claim 10.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1559 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 1..853

( x i ) SEQUENCE DESCRIPTION: SEQ ID NO:1:

```
CTG  ACC  GAG  CTG  GGT  GTG  CCG  ATC  GCC  CCA  TCG  ACC  TAC  TAC  GAC  CAC         48
Leu  Thr  Glu  Leu  Gly  Val  Pro  Ile  Ala  Pro  Ser  Thr  Tyr  Tyr  Asp  His
  1                  5                        10                       15

ATC  AAC  CGG  GAG  CCC  AGC  CGC  CGC  GAG  CTG  CGC  GAT  GGC  GAA  CTC  AAG         96
Ile  Asn  Arg  Glu  Pro  Ser  Arg  Arg  Glu  Leu  Arg  Asp  Gly  Glu  Leu  Lys
                    20                       25                       30

GAG  CAC  ATC  AGC  CGC  GTC  CAC  GCC  GCC  AAC  TAC  GGT  GTT  TAC  GGT  GCC        144
Glu  His  Ile  Ser  Arg  Val  His  Ala  Ala  Asn  Tyr  Gly  Val  Tyr  Gly  Ala
               35                       40                       45

CGC  AAA  GTG  TGG  CTA  ACC  CTG  AAC  CGT  GAG  GGC  ATC  GAG  GTG  GCC  AGA        192
Arg  Lys  Val  Trp  Leu  Thr  Leu  Asn  Arg  Glu  Gly  Ile  Glu  Val  Ala  Arg
          50                       55                       60

TGC  ACC  GTC  GAA  CGG  CTG  ATG  ACC  AAA  CTC  GGC  CTG  TCC  GGG  ACC  ACC        240
Cys  Thr  Val  Glu  Arg  Leu  Met  Thr  Lys  Leu  Gly  Leu  Ser  Gly  Thr  Thr
 65                       70                       75                       80

CGC  GGC  AAA  GCC  CGC  AGG  ACC  ACG  ATC  GCT  GAT  CCG  GCC  ACA  GCC  CGT        288
Arg  Gly  Lys  Ala  Arg  Arg  Thr  Thr  Ile  Ala  Asp  Pro  Ala  Thr  Ala  Arg
                    85                       90                       95

CCC  GCC  GAT  CTC  GTC  CAG  CGC  CGC  TTC  GGA  CCA  CCA  GCA  CCT  AAC  CGG        336
Pro  Ala  Asp  Leu  Val  Gln  Arg  Arg  Phe  Gly  Pro  Pro  Ala  Pro  Asn  Arg
               100                      105                      110

CTG  TGG  GTA  GCA  GAC  CTC  ACC  TAT  GTG  TCG  ACC  TGG  GCA  GGG  TTC  GCC        384
Leu  Trp  Val  Ala  Asp  Leu  Thr  Tyr  Val  Ser  Thr  Trp  Ala  Gly  Phe  Ala
          115                      120                      125

TAC  GTG  GCC  TTT  GTC  ACC  GAC  GCC  TAC  GCT  CGC  AGG  ATC  CTG  GGC  TGG        432
Tyr  Val  Ala  Phe  Val  Thr  Asp  Ala  Tyr  Ala  Arg  Arg  Ile  Leu  Gly  Trp
     130                      135                      140
```

```
CGG  GTC  GCT  TCC  ACG  ATG  GCC  ACC  TCC  ATG  GTC  CTC  GAC  GCG  ATC  GAG   480
Arg  Val  Ala  Ser  Thr  Met  Ala  Thr  Ser  Met  Val  Leu  Asp  Ala  Ile  Glu
145                      150                      155                      160

CAA  GCC  ATC  TGG  ACC  CGC  CAA  CAA  GAA  GGC  GTA  CTC  GAC  CTG  AAA  GAG   528
Gln  Ala  Ile  Trp  Thr  Arg  Gln  Gln  Glu  Gly  Val  Leu  Asp  Leu  Lys  Glu
                    165                      170                      175

GTT  ATC  CAC  CAT  ACG  GAT  AGG  GGA  TCT  CAG  TAC  ACA  TCG  ATC  CGG  TTC   576
Val  Ile  His  His  Thr  Asp  Arg  Gly  Ser  Gln  Tyr  Thr  Ser  Ile  Arg  Phe
               180                      185                      190

AGC  GAG  CGG  CTC  GCC  GAG  GCA  GGC  ATC  CAA  CCG  TCG  GTC  GGA  GCG  GTC   624
Ser  Glu  Arg  Leu  Ala  Glu  Ala  Gly  Ile  Gln  Pro  Ser  Val  Gly  Ala  Val
          195                      200                      205

GGA  AGC  TCC  TAT  GAC  AAT  GCA  CTA  GCC  GAG  ACG  ATC  AAC  GGC  CTA  TAC   672
Gly  Ser  Ser  Tyr  Asp  Asn  Ala  Leu  Ala  Glu  Thr  Ile  Asn  Gly  Leu  Tyr
     210                      215                      220

AAG  ACC  GAG  CTG  ATC  AAA  CCC  GGC  AAG  CCC  TGG  CGG  TCC  ATC  GAG  GAT   720
Lys  Thr  Glu  Leu  Ile  Lys  Pro  Gly  Lys  Pro  Trp  Arg  Ser  Ile  Glu  Asp
225                      230                      235                      240

GTC  GAG  TTG  GCC  ACC  GCG  CGC  TGG  GTC  GAC  TGG  TTC  AAC  CAT  CGC  CGC   768
Val  Glu  Leu  Ala  Thr  Ala  Arg  Trp  Val  Asp  Trp  Phe  Asn  His  Arg  Arg
                    245                      250                      255

CTC  TAC  CAG  TAC  TGC  GGC  GAC  GTC  CCG  CCG  GTC  GAA  CTC  GAG  GCT  GCC   816
Leu  Tyr  Gln  Tyr  Cys  Gly  Asp  Val  Pro  Pro  Val  Glu  Leu  Glu  Ala  Ala
               260                      265                      270

TAC  TAC  GCT  CAA  CGC  CAG  AGA  CCA  GCC  GCC  GGC  TGA  G GTCTCAGATC          863
Tyr  Tyr  Ala  Gln  Arg  Gln  Arg  Pro  Ala  Ala  Gly
          275                      280

AGAGAGTCTC  CGGACTCACC  GGGGCGGTTC  AGGCCCCGAT  GGTGTGCCCG  GTGGTGATAC    923

GGGCACACCA  GCACCAGGTT  GGCCAGCTCG  GTGGCCCCAC  CGTCCTGCCA  ATGTCGGATG    983

TGGTGGGCGT  GCAAACCCCG  GGTGGCCCCA  CAACCGGGAA  CCACACACGT  GCGGTCGCGA   1043

TGCTCAAGCG  CACGACGCAA  CCGACGATTG  ATCTGACGAG  TCGTTCGACC  GCAGCCAATG   1103

ACCTGCCCGT  CACGTTCAAA  CCAGGCCTCA  AGGTGGCAT   CACAGAGCAG  ATATCGGCGT   1163

TCGGACTCGC  TGAGCAGCGG  ACCCAGGTGC  AGGCCAGCGG  CACGCTCCTG  CACGTCTAGA   1223

TGCATCACCA  CGGTGGTGTG  CTGCCCATGT  GGCCGACGAG  CCACCTCGGC  GTCCCAGCCG   1283

GCCTCAACCA  GACGCAGAAA  CGCCTCAACA  TTGCCCGGCA  ACGGGGCCG   CTGATCCGAC   1343

ACACCGTCGC  TGTTGTCGTG  ATCACGCTTG  TACTCGGCGA  TCAACGCATC  CAGATGAGAC   1403

TGCAACGCCG  CATCGAACTT  CGCCGCCTCC  ACGTCGAAGC  TTGATTCGCC  AACAACTGAA   1463

CTGCTCATCG  GCGCTCCTGG  TGATCGAGGG  CCGCGGTTCC  GGCCGAAAAT  CCGGTTCGGG   1523

TTCGGGTCGC  GGTTCCAACT  TGAGCGCGGT  CCGCAG                               1559
```

(2) INFORMATION FOR SEQ ID NO:2:

(i) SEQUENCE CHARACTERISTICS:
        (A) LENGTH: 283 amino acids
        (B) TYPE: amino acid
        (D) TOPOLOGY: linear (ii) MOLECULE TYPE: protein (xi) SEQUENCE DESCRIPTION: SEQ ID NO:2:

```
Leu  Thr  Glu  Leu  Gly  Val  Pro  Ile  Ala  Pro  Ser  Thr  Tyr  Tyr  Asp  His
1                   5                        10                       15

Ile  Asn  Arg  Glu  Pro  Ser  Arg  Arg  Glu  Leu  Arg  Asp  Gly  Glu  Leu  Lys
               20                       25                       30

Glu  His  Ile  Ser  Arg  Val  His  Ala  Ala  Asn  Tyr  Gly  Val  Tyr  Gly  Ala
          35                       40                       45
```

| Arg | Lys | Val | Trp | Leu | Thr | Leu | Asn | Arg | Glu | Gly | Ile | Glu | Val | Ala | Arg |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Cys | Thr | Val | Glu | Arg | Leu | Met | Thr | Lys | Leu | Gly | Leu | Ser | Gly | Thr | Thr |
|-----|-----|-----|-----|-----|-----|-----|-----|-----|-----|-----|-----|-----|-----|-----|-----|
| 65  |     |     |     |     | 70  |     |     |     | 75  |     |     |     |     |     | 80  |

| Arg | Gly | Lys | Ala | Arg | Arg | Thr | Thr | Ile | Ala | Asp | Pro | Ala | Thr | Ala | Arg |
|     |     |     |     | 85  |     |     |     |     | 90  |     |     |     |     | 95  |     |

| Pro | Ala | Asp | Leu | Val | Gln | Arg | Arg | Phe | Gly | Pro | Pro | Ala | Pro | Asn | Arg |
|     |     |     |     | 100 |     |     |     | 105 |     |     |     |     | 110 |     |     |

| Leu | Trp | Val | Ala | Asp | Leu | Thr | Tyr | Val | Ser | Thr | Trp | Ala | Gly | Phe | Ala |
|     |     | 115 |     |     |     |     | 120 |     |     |     |     | 125 |     |     |     |

| Tyr | Val | Ala | Phe | Val | Thr | Asp | Ala | Tyr | Ala | Arg | Arg | Ile | Leu | Gly | Trp |
|     | 130 |     |     |     |     | 135 |     |     |     |     | 140 |     |     |     |     |

| Arg | Val | Ala | Ser | Thr | Met | Ala | Thr | Ser | Met | Val | Leu | Asp | Ala | Ile | Glu |
| 145 |     |     |     |     | 150 |     |     |     |     | 155 |     |     |     |     | 160 |

| Gln | Ala | Ile | Trp | Thr | Arg | Gln | Gln | Glu | Gly | Val | Leu | Asp | Leu | Lys | Glu |
|     |     |     |     | 165 |     |     |     |     | 170 |     |     |     |     | 175 |     |

| Val | Ile | His | His | Thr | Asp | Arg | Gly | Ser | Gln | Tyr | Thr | Ser | Ile | Arg | Phe |
|     |     |     | 180 |     |     |     |     | 185 |     |     |     |     | 190 |     |     |

| Ser | Glu | Arg | Leu | Ala | Glu | Ala | Gly | Ile | Gln | Pro | Ser | Val | Gly | Ala | Val |
|     |     | 195 |     |     |     |     | 200 |     |     |     |     | 205 |     |     |     |

| Gly | Ser | Ser | Tyr | Asp | Asn | Ala | Leu | Ala | Glu | Thr | Ile | Asn | Gly | Leu | Tyr |
|     | 210 |     |     |     |     | 215 |     |     |     |     | 220 |     |     |     |     |

| Lys | Thr | Glu | Leu | Ile | Lys | Pro | Gly | Lys | Pro | Trp | Arg | Ser | Ile | Glu | Asp |
| 225 |     |     |     |     | 230 |     |     |     |     | 235 |     |     |     |     | 240 |

| Val | Glu | Leu | Ala | Thr | Ala | Arg | Trp | Val | Asp | Trp | Phe | Asn | His | Arg | Arg |
|     |     |     |     | 245 |     |     |     |     | 250 |     |     |     |     | 255 |     |

| Leu | Tyr | Gln | Tyr | Cys | Gly | Asp | Val | Pro | Pro | Val | Glu | Leu | Glu | Ala | Ala |
|     |     |     | 260 |     |     |     |     | 265 |     |     |     |     | 270 |     |     |

| Tyr | Tyr | Ala | Gln | Arg | Gln | Arg | Pro | Ala | Ala | Gly |
|     |     | 275 |     |     |     |     | 280 |     |     |     |

(2) INFORMATION FOR SEQ ID NO:3:

(i) SEQUENCE CHARACTERISTICS:
        (A) LENGTH: 1358 base pairs
        (B) TYPE: nucleic acid
        (C) STRANDEDNESS: both
        (D) TOPOLOGY: linear (xi) SEQUENCE DESCRIPTION: SEQ ID NO:3:

```
CCTGAACCGC CCCGGCATGT CCGGAGACTC CAGTTCTTGG AAAGGATGGG GTCATGTCAG    60
GTGGTTCATC GAGGAGGTAC CCGCCGGAGC TGCGTGAGCG GGCGGTGCGG ATGGTCGCAG   120
AGATCCGCGG TCAGCACGAT TCGGAGTGGG CAGCGATCAG TGAGATCGCC CGTCTACTTG   180
GTGTTGCTGC GCGGAGACGG TGCGTAAGTG GGTGCGCCAG GCGCAGGTCG ATGCCGGCGC   240
ACGGCCCGGG ACCACGACCG AAGAATCCGC TGAGATAAAG CGCTTGCGGC GGGACAACGC   300
CGAATTGCGA AGGGCGAACG CGATTTTAAA GACCGCGTCG GCTTTCTTCG CGGCCGAGCT   360
CGACCGGCCA GCACGCTAAT TACCCGGTTC ATCGCCGATC ATCAGGGCCA CCGCGAGGGC   420
CCCGATGGTT TGCGGTGGGG TGTCGAGTCG ATCTGCACAC AGCTGACCGA GCTGGGTGTG   480
CCGATCGGCC CATCGACCTA CTACGACCAC ATCAACCGGG AGCCCAGCCG CCGCGAGCTG   540
CGCGATGGCG AACTCAAGGA GCACATCAGC CGCGTCCACG CCGCCAACTA CGGTGTTTAC   600
GGTGCCCGCA AAGTGTGGCT AACCCTGAAC CGTGAGGGCA TCGAGGTGGC CAGATGCACC   660
GTCGAACGGC TGATGACCAA ACTCGGCCTG TCCGGGACCA CCCGCGGCAA AGCCCGCAGG   720
```

```
ACCACGATCG CTGATCCGGC CACAGCCCGT CCCGCCGATC TCGTCCAGCG CCGCTTCGGA      780

CCACCAGCAC CTAACCGGCT GTGGGTAGCA GACCTCACCT ATGTGTCGAC CTGGGCAGGG      840

TTCGCCTACG TGGCCTTTGT CACCGACGCC TACGCTCGCA GGATCCTGGG CTGGCGGGTC      900

GCTTCCACGA TGGCCACCTC CATGGTCCTC GACGCGATCG AGCAAGCCAT CTGGACCCGC      960

CAACAAGAAG GCGTACTCGA CCTGAAAGAC GTTATCCACC ATACGGATAG GGATCTCAG     1020

TACACATCGA TCCGGTTCAG CGAGCGGCTC GCCGAGGCAG GCATCCAACC GTCGGTCGGA     1080

GCGGTCGGAA GCTCCTATGA CAATGCACTA GCCGAGACGA TCAACGGCCT ATACAAGACC     1140

GAGCTGATCA AACCCGGCAA GCCCTGGCGG TCCATCGAGG ATGTCGAGTT GGCCACCGCG     1200

CGCTGGGTCG ACTGGTTCAA CCATCGCCGC CTCTACCAGT ACTGCGGCGA CGTCCCGCCG     1260

GTCGAACTCG AGGCTGCCTA CTACGCTCAA CGCCAGAGAC CAGCCGCCGG CTGAGGTCTC     1320

AGATCAGAGA GTCTCCGGAC TCACCGGGGC GGTTCAGG                             1358
```

( 2 ) INFORMATION FOR SEQ ID NO:4:

( i ) SEQUENCE CHARACTERISTICS:
        ( A ) LENGTH: 278 amino acids
        ( B ) TYPE: amino acid
        ( D ) TOPOLOGY: unknown ( x i ) SEQUENCE DESCRIPTION: SEQ ID NO:4:

```
Val Pro Ile Ala Pro Ser Thr Tyr Tyr Asp His Ile Asn Arg Glu Pro
 1               5                  10                  15

Ser Arg Arg Glu Leu Arg Asp Gly Glu Leu Lys Glu His Ile Ser Arg
                20                  25                  30

Val His Ala Ala Asn Tyr Gly Val Tyr Gly Ala Arg Lys Val Trp Leu
            35                  40                  45

Thr Leu Asn Arg Glu Gly Ile Glu Val Ala Arg Cys Thr Val Glu Arg
        50                  55                  60

Leu Met Thr Lys Leu Gly Leu Ser Gly Thr Thr Arg Gly Lys Ala Arg
65                  70                  75                  80

Arg Thr Thr Ile Ala Asp Pro Ala Thr Ala Arg Pro Ala Asp Leu Val
                85                  90                  95

Gln Arg Arg Phe Gly Pro Pro Ala Pro Asn Arg Leu Trp Val Ala Asp
            100                 105                 110

Leu Thr Tyr Val Ser Thr Trp Ala Gly Phe Ala Tyr Val Ala Phe Val
        115                 120                 125

Thr Asp Ala Tyr Ala Arg Arg Ile Leu Gly Trp Arg Val Ala Ser Thr
    130                 135                 140

Met Ala Thr Ser Met Val Leu Asp Ala Ile Glu Gln Ala Ile Trp Thr
145                 150                 155                 160

Arg Gln Gln Glu Gly Val Leu Asp Leu Lys Asp Val Ile His His Thr
                165                 170                 175

Asp Arg Gly Ser Gln Tyr Thr Ser Ile Arg Phe Ser Glu Arg Leu Ala
            180                 185                 190

Glu Ala Gly Ile Gln Pro Ser Val Gly Ala Val Gly Ser Ser Tyr Asp
        195                 200                 205

Asn Ala Leu Ala Glu Thr Ile Asn Gly Leu Tyr Lys Thr Glu Leu Ile
    210                 215                 220

Lys Pro Gly Lys Pro Trp Arg Ser Ile Glu Asp Val Glu Leu Ala Thr
225                 230                 235                 240

Ala Arg Trp Val Asp Trp Phe Asn His Arg Arg Leu Tyr Gln Tyr Cys
                245                 250                 255
```

```
Gly  Asp  Val  Pro  Pro  Val  Glu  Leu  Glu  Ala  Ala  Tyr  Tyr  Ala  Gln  Arg
               260            265                      270

Gln  Arg  Pro  Ala  Ala  Gly
          275
```

( 2 ) INFORMATION FOR SEQ ID NO:5:

( i ) SEQUENCE CHARACTERISTICS:
        ( A ) LENGTH: 188 amino acids
        ( B ) TYPE: amino acid
        ( D ) TOPOLOGY: unknown ( x i ) SEQUENCE DESCRIPTION: SEQ ID NO:5:

```
Met  Met  Pro  Leu  Leu  Asp  Lys  Leu  Arg  Glu  Gln  Tyr  Gly  Val  Gly  Pro
1              5                        10                       15

Leu  Cys  Ser  Glu  Leu  His  Ile  Ala  Pro  Ser  Thr  Tyr  Tyr  His  Cys  Gln
               20                       25                       30

Gln  Gln  Arg  His  His  Pro  Asp  Lys  Arg  Ser  Ala  Arg  Ala  Gln  Arg  Asp
          35                       40                  45

Asp  Trp  Leu  Lys  Lys  Gln  Ile  Gln  Arg  Val  Tyr  Asp  Glu  Asn  His  Lys
          50                       55                  60

Val  Tyr  Gly  Val  Arg  Lys  Val  Trp  Arg  Gln  Leu  Leu  Arg  Glu  Gly  Ile
65                       70                  75                            80

Arg  Val  Ala  Arg  Cys  Thr  Val  Ala  Arg  Leu  Met  Ala  Val  Met  Gly  Leu
               85                       90                       95

Ala  Gly  Val  Leu  Arg  Gly  Lys  Lys  Val  Arg  Thr  Thr  Ile  Ser  Arg  Lys
               100                      105                      110

Ala  Val  Ala  Ala  Gly  His  Arg  Val  Asn  Arg  Gln  Phe  Val  Ala  Glu  Arg
               115                      120                      125

Pro  Asp  Gln  Leu  Trp  Val  Ala  Asp  Phe  Thr  Tyr  Val  Ser  Thr  Trp  Arg
     130                      135                 140

Gly  Phe  Val  Tyr  Val  Ala  Phe  Ile  Ile  Asp  Val  Phe  Ala  Gly  Tyr  Ile
145                           150                 155                      160

Val  Gly  Trp  Arg  Val  Ser  Ser  Ser  Met  Glu  Thr  Thr  Phe  Val  Leu  Asp
               165                      170                      175

Ala  Leu  Glu  Gln  Ala  Leu  Trp  Thr  Arg  Arg  Pro  Pro
               180                      185
```

( 2 ) INFORMATION FOR SEQ ID NO:6:

( i ) SEQUENCE CHARACTERISTICS:
        ( A ) LENGTH: 288 amino acids
        ( B ) TYPE: amino acid
        ( D ) TOPOLOGY: unknown ( x i ) SEQUENCE DESCRIPTION: SEQ ID NO:6:

```
Met  Lys  Tyr  Val  Phe  Ile  Glu  Lys  His  Gln  Ala  Glu  Phe  Ser  Ile  Lys
1              5                        10                       15

Ala  Met  Cys  Arg  Val  Leu  Arg  Val  Ala  Arg  Ser  Gly  Trp  Tyr  Thr  Trp
               20                       25                       30

Cys  Gln  Arg  Arg  Thr  Arg  Ile  Ser  Thr  Arg  Gln  Gln  Phe  Arg  Gln  His
          35                       40                  45

Cys  Asp  Ser  Val  Val  Leu  Ala  Ala  Phe  Thr  Arg  Ser  Lys  Gln  Arg  Tyr
          50                       55                  60

Gly  Ala  Pro  Arg  Leu  Thr  Asp  Glu  Leu  Arg  Ala  Gln  Gly  Tyr  Pro  Phe
65                       70                  75                            80

Asn  Val  Lys  Thr  Val  Ala  Ala  Ser  Leu  Arg  Arg  Gln  Gly  Leu  Arg  Ala
               85                       90                       95
```

-continued

```
Lys Ala Ser Arg Lys Phe Ser Pro Val Ser Tyr Arg Ala His Gly Leu
            100             105                 110

Pro Val Ser Glu Asn Leu Leu Glu Gln Asp Phe Tyr Ala Ser Gly Pro
        115             120             125

Asn Gln Lys Trp Ala Gly Asp Ile Thr Tyr Leu Arg Thr Asp Glu Gly
    130             135             140

Trp Leu Tyr Leu Ala Val Val Ile Asp Leu Trp Ser Arg Ala Val Ile
145                 150             155                         160

Gly Trp Ser Met Ser Pro Arg Met Thr Ala Gln Leu Ala Cys Asp Ala
                165             170             175

Leu Gln Met Ala Leu Trp Arg Arg Lys Arg Pro Arg Asn Val Ile Val
            180             185             190

His Thr Asp Arg Gly Gly Gln Tyr Cys Ser Ala Asp Tyr Gln Ala Gln
        195             200             205

Leu Lys Arg His Asn Leu Arg Gly Ser Met Ser Ala Lys Gly Cys Cys
    210             215             220

Tyr Asp Asn Ala Cys Val Glu Ser Phe Phe His Ser Leu Lys Val Glu
225                 230             235                         240

Cys Ile His Gly Glu His Phe Ile Ser Arg Glu Ile Met Arg Ala Thr
                245             250             255

Val Phe Asn Tyr Ile Glu Cys Asp Tyr Asn Arg Trp Arg Arg His Ser
            260             265             270

Trp Cys Gly Gly Leu Ser Pro Glu Gln Phe Glu Asn Lys Asn Leu Ala
        275             280             285
```

( 2 ) INFORMATION FOR SEQ ID NO:7:

( i ) SEQUENCE CHARACTERISTICS:
        ( A ) LENGTH: 272 amino acids
        ( B ) TYPE: amino acid
        ( D ) TOPOLOGY: unknown ( x i ) SEQUENCE DESCRIPTION: SEQ ID NO:7:

```
Met Cys Gln Val Phe Gly Val Ser Arg Ser Gly Tyr Tyr Asn Trp Val
1               5                   10                  15

Gln His Glu Pro Ser Asp Arg Lys Gln Ser Asp Glu Arg Leu Lys Leu
            20                  25                  30

Glu Ile Lys Val Ala His Ile Arg Thr Arg Glu Thr Tyr Gly Thr Arg
        35                  40                  45

Arg Leu Gln Thr Glu Leu Ala Glu Asn Gly Ile Ile Val Gly Arg Asp
    50                  55                  60

Arg Leu Ala Arg Leu Arg Lys Glu Leu Arg Leu Arg Cys Lys Gln Lys
65                  70                  75                      80

Arg Lys Phe Arg Ala Thr Thr Asn Ser Asn His Asn Leu Pro Val Ala
                85                  90                  95

Pro Asn Leu Leu Asn Gln Thr Phe Ala Pro Thr Ala Pro Asn Gln Val
            100                 105                 110

Trp Val Ala Asp Leu Thr Tyr Val Ala Thr Gln Glu Gly Trp Leu Tyr
        115                 120                 125

Leu Ala Gly Ile Lys Asp Val Tyr Thr Cys Glu Ile Val Arg Tyr Ala
    130                 135                 140

Met Gly Glu Arg Met Thr Lys Glu Leu Thr Gly Lys Ala Leu Phe Met
145                 150                 155                     160

Ala Leu Arg Ser Gln Arg Pro Pro Ala Gly Leu Ile His His Ser Asp
                165                 170                 175
```

```
Arg  Gly  Ser  Gln  Tyr  Cys  Ala  Tyr  Asp  Tyr  Arg  Val  Ile  Gln  Glu  Gln
               180                      185                    190

Ser  Gly  Leu  Lys  Thr  Ser  Met  Ser  Arg  Lys  Gly  Asn  Cys  Tyr  Asp  Asn
          195                      200                    205

Ala  Pro  Met  Glu  Ser  Phe  Trp  Gly  Thr  Leu  Lys  Asn  Glu  Ser  Leu  Ser
     210                      215                    220

His  Tyr  Arg  Phe  Asn  Asn  Arg  Asp  Glu  Ala  Ile  Ser  Val  Ile  Arg  Glu
225                      230                    235                         240

Tyr  Ile  Glu  Ile  Phe  Tyr  Asn  Arg  Gln  Arg  His  Ser  Arg  Leu  Gly
                    245                      250                    255

Asn  Ile  Ser  Pro  Ala  Ala  Phe  Arg  Glu  Lys  Tyr  His  Gln  Met  Ala  Ala
                    260                      265                    270
```

(2) INFORMATION FOR SEQ ID NO:8:

(i) SEQUENCE CHARACTERISTICS:
    (A) LENGTH: 44 amino acids
    (B) TYPE: amino acid
    (D) TOPOLOGY: unknown (xi) SEQUENCE DESCRIPTION: SEQ ID NO:8:

```
Met  Ser  Gly  Gly  Ser  Ser  Arg  Arg  Tyr  Pro  Pro  Glu  Leu  Arg  Glu  Arg
1                        5                      10                         15

Ala  Val  Arg  Met  Val  Ala  Glu  Ile  Arg  Gly  Gln  His  Asp  Ser  Glu  Trp
               20                      25                    30

Ala  Ala  Ile  Ser  Glu  Ile  Ala  Arg  Leu  Leu  Gly  Val
               35                      40
```

(2) INFORMATION FOR SEQ ID NO:9:

(i) SEQUENCE CHARACTERISTICS:
    (A) LENGTH: 63 amino acids
    (B) TYPE: amino acid
    (D) TOPOLOGY: unknown (xi) SEQUENCE DESCRIPTION: SEQ ID NO:9:

```
Cys  Ala  Glu  Thr  Val  Arg  Lys  Trp  Val  Arg  Gln  Ala  Gln  Val  Asp  Ala
1                        5                      10                         15

Gly  Ala  Arg  Pro  Gly  Thr  Thr  Thr  Glu  Glu  Ser  Ala  Glu  Ile  Lys  Arg
               20                      25                    30

Leu  Arg  Arg  Asp  Asn  Ala  Glu  Leu  Arg  Arg  Ala  Asn  Ala  Ile  Leu  Lys
          35                      40                    45

Thr  Ala  Ser  Ala  Phe  Phe  Ala  Ala  Glu  Leu  Asp  Arg  Pro  Ala  Arg
          50                      55                    60
```

(2) INFORMATION FOR SEQ ID NO:10:

(i) SEQUENCE CHARACTERISTICS:
    (A) LENGTH: 108 amino acids
    (B) TYPE: amino acid
    (D) TOPOLOGY: unknown (xi) SEQUENCE DESCRIPTION: SEQ ID NO:10:

```
Met  Thr  Lys  Asn  Thr  Arg  Phe  Ser  Pro  Glu  Val  Arg  Gln  Arg  Ala  Val
1                        5                      10                         15

Arg  Met  Val  Leu  Glu  Ser  Gln  Ser  Glu  Tyr  Asp  Ser  Gln  Trp  Ala  Thr
               20                      25                    30

Ile  Cys  Ser  Ile  Ala  Pro  Lys  Ile  Gly  Cys  Thr  Arg  Glu  Thr  Leu  Arg
          35                      40                    45

Val  Trp  Val  Arg  Gln  His  Glu  Arg  Asp  Thr  Gly  Gly  Gly  Asp  Gly  Gly
          50                      55                    60
```

```
              Leu   Thr   Thr   Ala   Glu   Arg   Gln   Arg   Leu   Lys   Glu   Leu   Glu   Arg   Glu   Asn
              65                      70                        75                              80

Arg   Glu   Leu   Arg   Arg   Ser   Asn   Asp   Ile   Leu   Arg   Gln   Ala   Ser   Ala   Tyr
                                      85                        90                              95

Phe   Ala   Lys   Ala   Glu   Phe   Asp   Arg   Leu   Trp   Lys   Lys
                                      100                       105
```

( 2 ) INFORMATION FOR SEQ ID NO:11:

( i ) SEQUENCE CHARACTERISTICS:
        ( A ) LENGTH: 99 amino acids
        ( B ) TYPE: amino acid
        ( D ) TOPOLOGY: unknown ( x i ) SEQUENCE DESCRIPTION: SEQ ID NO:11:

```
              Met   Thr   Lys   Thr   Val   Ser   Thr   Ser   Lys   Lys   Pro   Arg   Lys   Gln   His   Ser
              1                       5                         10                              15

Pro   Glu   Phe   Arg   Ser   Glu   Ala   Leu   Lys   Leu   Ala   Glu   Arg   Ile   Gly   Val
                                      20                        25                              30

Thr   Ala   Ala   Ala   Arg   Glu   Leu   Ser   Leu   Tyr   Glu   Ser   Gln   Leu   Tyr   Asn
                                      35                        40                              45

Trp   Arg   Ser   Lys   Gln   Gln   Asn   Gln   Gln   Thr   Ser   Ser   Glu   Arg   Glu   Leu
                    50                                55                              60

Glu   Met   Ser   Thr   Glu   Ile   Ala   Arg   Leu   Lys   Arg   Gln   Leu   Ala   Glu   Arg
              65                      70                        75                              80

Asp   Glu   Glu   Leu   Ala   Ile   Leu   Gln   Lys   Ala   Ala   Thr   Tyr   Phe   Ala   Lys
                                      85                        90                              95

Arg   Leu   Lys
```

( 2 ) INFORMATION FOR SEQ ID NO:12:

( i ) SEQUENCE CHARACTERISTICS:
        ( A ) LENGTH: 100 amino acids
        ( B ) TYPE: amino acid
        ( D ) TOPOLOGY: unknown ( x i ) SEQUENCE DESCRIPTION: SEQ ID NO:12:

```
              Met   Ser   Arg   Lys   Thr   Gln   Arg   Tyr   Ser   Lys   Glu   Phe   Lys   Ala   Glu   Ala
              1                       5                         10                              15

Val   Arg   Thr   Val   Pro   Glu   Asn   Gln   Leu   Ser   Ile   Ser   Glu   Gly   Ala   Ser
                                      20                        25                              30

Arg   Leu   Ser   Leu   Pro   Glu   Gly   Thr   Leu   Gly   Gln   Trp   Val   Thr   Ala   Ala
                                35                            40                        45

Arg   Lys   Gly   Leu   Gly   Thr   Pro   Gly   Ser   Arg   Thr   Val   Ala   Glu   Leu   Glu
                          50                            55                      60

Ser   Glu   Ile   Leu   Gln   Leu   Arg   Lys   Ala   Leu   Asn   Glu   Ala   Arg   Leu   Glu
              65                      70                        75                              80

Arg   Asp   Ile   Leu   Lys   Lys   Ala   Thr   Ala   Tyr   Phe   Ala   Gln   Glu   Ser   Leu
                                      85                        90                              95

Lys   Asn   Thr   Arg
                                100
```

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:13:

TGAACCGCCC CGGCATGTCC GGAGACTC                                                                           2 8

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:14:

TGAACCGCCC CGGGAATCCT GGAGACT                                                                            2 7

( 2 ) INFORMATION FOR SEQ ID NO:15:

( i ) SEQUENCE CHARACTERISTICS:
        ( A ) LENGTH: 94 amino acids
        ( B ) TYPE: amino acid
        ( D ) TOPOLOGY: unknown ( x i ) SEQUENCE DESCRIPTION: SEQ ID NO:15:

```
Gly  Thr  Val  His  His  Ser  Asp  Lys  Gly  Ser  Gln  Tyr  Val  Ser  Leu  Ala
1                   5                        10                       15

Tyr  Thr  Gln  Arg  Leu  Lys  Glu  Ala  Gly  Leu  Leu  Ala  Ser  Thr  Gly  Ser
               20                        25                       30

Thr  Gly  Asp  Ser  Tyr  Asp  Asn  Ala  Met  Ala  Glu  Ser  Ile  Asn  Gly  Leu
          35                        40                       45

Tyr  Lys  Ala  Glu  Val  Ile  His  Arg  Lys  Ser  Trp  Lys  Asn  Arg  Ala  Glu
     50                        55                       60

Val  Glu  Leu  Ala  Thr  Leu  Thr  Trp  Val  Asp  Trp  Tyr  Asn  Asn  Arg  Arg
65                        70                       75                       80

Leu  Leu  Glu  Arg  Leu  Gly  His  Thr  Pro  Pro  Ala  Glu  Ala  Glu
                    85                   90
```

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:16:

TGAACCGCCC CGGTGAGTCC GGAGACTC                                                                           2 8

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:17:

TGAACCGCCC CGGGTTTCCT GGAGAGT                                                                            2 7